(12) United States Patent
Berggren et al.

(10) Patent No.: US 8,715,478 B2
(45) Date of Patent: May 6, 2014

(54) ELECTRICALLY CONTROLLED ION TRANSPORT DEVICE

(75) Inventors: Rolf Magnus Berggren, Vreta Kloster (SE); Joakim Isaksson, Waalre (NL); Edwin Jager, Linköping (SE); Peter Kjäll, Lidingö (SE); David Nilsson, Vikingstad (SE); Agneta Richter Dahlfors, Saltsio-Boo (SE); Daniel T. Simon, Linköping (SE); Klas Tybrandt, Linköping (SE)

(73) Assignee: Oboe IPR AB, Norrkopoing (SE)

( * ) Notice: Subject to any disclaimer, the term of this patent is extended or adjusted under 35 U.S.C. 154(b) by 704 days.

(21) Appl. No.: 12/745,935

(22) PCT Filed: Dec. 3, 2008

(86) PCT No.: PCT/SE2008/000682
§ 371 (c)(1),
(2), (4) Date: Jun. 3, 2010

(87) PCT Pub. No.: WO2009/072952
PCT Pub. Date: Jun. 11, 2009

(65) Prior Publication Data
US 2010/0255557 A1   Oct. 7, 2010

Related U.S. Application Data

(60) Provisional application No. 60/996,735, filed on Dec. 3, 2007.

(30) Foreign Application Priority Data

Dec. 3, 2007 (EP) .................................... 07122186

(51) Int. Cl.
*G01N 27/453* (2006.01)
(52) U.S. Cl.
USPC .......................................... 204/600; 204/601
(58) Field of Classification Search
USPC .................. 204/600, 601, 450, 451, 550; 435/173.6, 285.2; 600/20; 604/20
See application file for complete search history.

(56) References Cited

U.S. PATENT DOCUMENTS 5,711,761 A * 1/1998 Untereker et al. ............... 604/20
7,164,943 B2 * 1/2007 Roy ................................ 604/20
(Continued)

FOREIGN PATENT DOCUMENTS

EP           1 862 799 A     12/2007
WO      2005/053836 A        6/2005

OTHER PUBLICATIONS

Isaksson, J et al. Electronic control of Ca2+ signalling in neuronal cells using an organic electronic ion pump. Nature Materials. 2007. 6(9): 673-679. Published online Jul. 22, 2007.*

(Continued)

*Primary Examiner* — Alex Noguerola
(74) *Attorney, Agent, or Firm* — Maier & Maier, PLLC

(57) ABSTRACT

A device for electrically controlled transport of ions between a source and a target electrolyte, including: a first source electrode and a first target electrode, each capable of conducting ions and electrons, wherein the source electrode is arranged to receive ions from the source electrolyte and the target electrode is arranged to release ions to the target electrolyte.

15 Claims, 20 Drawing Sheets

(56) References Cited

U.S. PATENT DOCUMENTS

| | | | |
|---|---|---|---|
| 7,857,759 B2* | 12/2010 | Asano et al. | 600/365 |
| 8,137,524 B2* | 3/2012 | Berggren et al. | 204/630 |

OTHER PUBLICATIONS

Chandrasekhar, Prasanna, "Conducting Polymers, Fundamentals and Applications, A Practical Approach", Kluwer Academic Publishers, Boston, 1999, p. Nos. 544-562, 22 pages total.

Berggren, Magnus et al., "Organic Bioelectronics", Advanced Materials, Wiley Inter-Science, 2007, p. Nos. 3201-3213, 13 pages total.

Epstein, Arthur, "Novel Concepts in Electronic Polymers: Polyaniline and Its Derivatives", Makromol. Chem., Macromol. Symp. 51, 217-234, 1991, p. Nos. 217-234 pages, 18 pages total.

Schottland, Philippe et al., "Poly (3,4-alkylenedioxypyrrole)s: Highly Stable Electronically Conducting and Electrochromic Polymers", Macromolecules, 33, 2000, p. Nos. 7051-7061, 11 pages total.

Onoda, Mitsuyoshi et al., "Properties of Electrochemically Cation-Doped Poly(isothianaphthene)", J. Electrochem. Soc., vol. 141, No. 2, Feb. 1994, p. Nos. 338-341, 4 pages total.

Cohen, Edward et al., "Modern Coating and Drying Technology", VCH Publishers, Inc., 1992, p. Nos. 1-21, 28 pages total.

Gustafsson, J.C. et al., "In Situ Spectroscopic Investigations of Electrochromism and Ion Transport in a Poly (3, 4-ethylenedioxythiophene) Electrode in a Solid State Electrochemical Cell", Solid State Ionics 69, 1994, p. Nos. 145-152, 8 pages total.

Fichou, Denis, "Handbook of Oligo- and Polythiophenes", Wiley-VCH, Weinheim, 1999, p. Nos. 491-524, 36 pages total.

Office Action dated Feb. 3, 2010 issued by the European Patent Office to corresponding European Patent Application No. 07122186.5, 1 page.

Office Action dated Jul. 2, 2010 issued by the European Patent Office to corresponding European Patent Application No. 07122186.5, 2 pages.

Jun. 24, 2010 Response as filed with the European Patent Office to corresponding European Patent Application No. 07122186.5, 29 pages.

International Search Report dated Jan. 13, 2009 to corresponding international patent application No. PCT/SE2008/000682, 4 pages.

European Search Report dated Jun. 4, 2008 to corresponding priority application No. EP 07 12 2186, 2 pages.

Isaksson, Joakim et al., "Electronic Control of Ca2+ Signalling in Neuronal Cells Using an Organic Electronic Ion Pump", Nature Materials, vol. 6, No. 9, Jul. 22, 2007, pp. 673-679, XP002482909, ISSN: 1476-1122, Figure 2.

* cited by examiner

ELECTRICALLY CONTROLLED ION TRANSPORT DEVICE

RELATED APPLICATIONS

This application claims priority, under 35 U.S.C. §119, to international patent application No.: PCT/SE2008/000682, filed on Dec. 3, 2008, which claims priority to European patent application No.: 07122186.5, filed Dec. 3, 2007 and U.S. provisional patent application No. 60/996,735, filed on Dec. 3, 2007, the disclosures of which are incorporated by reference herein in their entireties.

FIELD OF THE INVENTION

The present invention relates to a device for electrically controlled transport of ions between a source and a target electrolyte, and to an apparatus for transporting ions to or from a cell. The present invention further relates to the use of such a device for transporting ions to or from a cell, and to methods of operating such a device.

BACKGROUND

Ion signaling in eukaryotic cells is essential for numerous physiological processes, including regulation of exocytosis, contraction, gene transcription and fertilization, as well as maintenance of cell membrane potential. Ion signaling is equally important in prokaryotic cells, e.g. in osmoregulation. Ion signaling in cells may be affected by alteration of extracellular and intracellular concentration of ions. Such alterations result in intracellular concentration changes in the forms of i) rapid increase followed by a rapid decrease (termed spikes), ii) a sustained, elevated concentration, or iii) repetitive spikes that produce an oscillation of characteristic frequency and amplitude. Due to technical limitations of available methods to decipher these complex signaling pathways, very little is known about the molecular and physiological effects on cells. A limitation of certain concern is the inability of available methods to provide controlled ion fluxes to cells to be studied.

Presently, transport of ions from, to or between electrolytes, such as from a stock solution to a cell culture medium, is performed by manual or automated use of e.g. pipettes, pumps or membranes. Such techniques result in unspecific delivery of ions to a cell culture medium as such only, whereas further diffusion to cells cultured in the medium is uncontrollable and unpredictable. Furthermore, said techniques require the use of expensive equipment. Examples of present methods for transport of ions are given below.

U.S. Pat. No. 6,780,584 discloses a device for the modulation of a reaction comprising: a first buffer reservoir containing a first buffer and a first charged entity, wherein the first buffer has an initial conductance less than 1000 μS/cm; a second buffer reservoir separated from the first buffer reservoir containing a second buffer comprising a second charged entity, wherein the second charged entity has a charge opposite that of the first charged entity, the second charged entity modulates the specific reaction between the specific binding entity and the first charged entity; a conductive semi permeable matrix contained in a non-conductive support material, the conductive semi permeable matrix disposed between and fluidically connecting the first buffer reservoir and the second buffer reservoir; a first electrode linked to a power source and located in the first buffer reservoir and contacting the first buffer; and a second electrode linked to the power source and located in the second buffer reservoir and contacting the second buffer; and a specific binding entity which reacts specifically with the first charged entity and which is physically fixed on, in, or adjacent to the semi permeable matrix.

U.S. Pat. No. 5,776,325 discloses a method of inducing mono-directional transport of ions between electrolyte solutions comprising separating the electrolyte solutions with a conducting polymer membrane and creating a potential gradient across said membrane wherein the potential gradient is created by using the conducting polymer membrane as a shared working electrode.

SUMMARY OF THE INVENTION

An object of the present invention is to provide a device which is capable of transporting ions of one or several ionic species from one or several source electrolytes to one or several target electrolytes, in which device the ion transport can be electrically controlled, and in which ions from one or several source electrolytes may be delivered to one or several target electrolytes in a space and time resolved manner.

A further object of the present invention is to provide a device that may be used in cell communication research. In such a device, controlled ion fluxes to, or from, cells to be studied are achieved by means of the inventive device in its ability to transport ions in a time and space resolved manner. Ion fluxes of even higher specificity may be provided by means of e.g. matrix addressing of inventive devices for the delivery of ions to, or removal of ions from, clusters of cells, single cells or in the sub-cellular scale. Accordingly, an additional object of the present invention is to provide use of the inventive device in cell communication research.

Yet another object of the invention is to provide a device which allows stimulating a single cell with a spatial resolution which allows different portions of said single cell to be stimulated simultaneously or consecutively by one or several ionic species.

Yet another object of the invention is to provide devices for matrix addressing for delivery of ions.

A further object of the present invention is to provide a device for cell communication research by electrically controlled ion transport, which device can be deposited on a wide range of different rigid or flexible substrates by conventional printing methods.

The above-mentioned objects, as well as further objects of the invention, which should be apparent to a person skilled in the art after having studied the description below, are achieved by the different aspects of the present invention as described herein.

According to a first aspect thereof, the invention relates to a device for electrically controlled transport of ions between a source and a target electrolyte, comprising:
- a first source electrode and a first target electrode, each capable of conducting ions and electrons, wherein said source electrode is arranged to receive ions from said source electrolyte and said target electrode is arranged to release ions to said target electrolyte, and
- means for retaining one of said source and target electrolytes on the device, which means are arranged such that the electrolyte is in contact with one of said electrodes, and
- a first ion-conductive channel, arranged to receive ions from said source electrode, to release ions to said target electrode and to provide an ionic connection between said source and said target electrodes,
wherein said electrodes and said ion-conductive channel are formed of solid or semi-solid materials which are directly or indirectly attached to a support, further comprising means for limiting an electronic current between said source and said target electrodes, such that at least after a voltage is applied across said channel a potential difference between said source and target electrodes is maintained, which effects ion transport from said source to said target electrode, and
wherein the cross-sectional area of the interface between said ion-conductive channel and one of said electrodes is within the range of about 1 nm$^2$ to about 10 mm$^2$.

By decreasing the cross sectional surface of the ion conductive channel and the electrode, a higher spatial accuracy of the delivery of the ions may be achieved—as the spatial distribution of the ions in the electrode will be more confined the smaller the interface.

Further, the cross section area of the ion conductive channels may also be used to determine the speed at which the ions are to pass to or from the electrodes. Hence, also the speed at which the ions are to be received from or released to the electrolyte.

In relation to this invention the electrode comprises three portions:
 an electrochemically active portion, the surface of which is arranged in ionic contact with an adjacent source or target electrolyte,
 an ion transport portion, which is arranged of ionically conductive material and which ionically connects the ion-conductive channel and said adjacent source of target electrolyte,
 an ion passage surface, which is the surface of said ion transport portion through which ions may pass to or from the electrolyte, i.e. a portion of the electrode which is both ionically conductive and arranged in direct contact with the electrolyte.

In relation to this invention the first ion-conductive channel extends between said source and target electrode, such that these are ionically connected.

The interface between the ion conductive channel and the electrode is normally the ion conductive surface area, which is orthogonal to the average direction of the ion flow between the source and the target electrodes, this is also referred to as the ion transport interface.

According to one embodiment the surface area of the interface between the ion conductive channel and the electrode is within the range of about 1 nm$^2$ to about 10 mm$^2$, or within the range of 5 nm$^2$ to about 100 μm$^2$, or within the range of 5 nm$^2$ to about 1 μm$^2$, or within the range of 10 nm$^2$ to about 1 μm$^2$, or within the range of 50 nm$^2$ to about 10 μm$^2$.

According to one embodiment, the ion passage surface area of one of said electrodes is within the range of about 1 nm$^2$ to about 10 mm$^2$ or 10 cm$^2$, or within the range of 5 nm$^2$ to about 100 μm$^2$, or within the range of 5 nm$^2$ to about 1 μm$^2$, or within the range of 10 nm$^2$ to about 1 μm$^2$, or within the range of 50 nm$^2$ to about 10 μm$^2$. A smaller ion passage surface area has the advantage of allowing a more accurate distribution of ions in terms of volumes and spatial distribution, compared to larger channels.

In some embodiment the electronic conductivity of the ion isolative means is limited or essentially none, in order to substantially isolate two elements electronically from each other. Hence, means for prevention of undesired electronic currents in the device is provided. In parts of this description the words insulation or insulation layer is used to denote e.g. the ion isolative means.

According to one embodiment, the device further comprises ion isolative means covering a surface portion of the ion conductive channel. In relation to this document ion isolative means comprises a material with non or limited ability to conduct ions. The ion isolative means may be arranged such that it defines, partially or wholly, the spacial extension of said ion passage surface. The use of ion isolative means has the advantage of facilitating a more accurate determination of where the ions are released to or received from the electrolyte. In other words, by sandwiching an isolating between the ion conductive material and the electrolyte, the ions may be distributed in a confined spot within the electrolyte. Thus, according to one embodiment, said means for retaining the electrolyte is arranged to retain the electrolyte in such a manner that at least a portion of the ion isolative means is sandwiched between the ion conductive channel and the electrolyte.

According to one embodiment, the ion passage surface, and hence the extension of the electrode, is defined by an ion isolative material which covers only a portion of an ion conductive and electrochemically active material. The ion isolative means may e.g. be arranged as a sheet or layer provided with an aperture or recess. The isolative means is preferably sandwiched between the electrolyte and the ion conductive and electrochemically active material, thereby defining the extension of the ion passage area and hence also the electrode. Moreover, the electrolyte is preferably arranged to cover at least a portion of said ion isolative material, and to be in physical contact with a portion of said ion conductive and electrochemically active material free of said ion isolative material.

Defining the ion passage surface by ion isolative means is advantageous as it permit a more accurate control of the point of delivery or reception of ions to or from the electrolyte, respectively. It also allows ions to be received or delivered not only at the edge or border, of the surface covered by electrolyte, closest to the ion conductive channel—but essentially anywhere within the electrolyte. This is advantageous as e.g. it enables a distribution of ions to two different portions of a cell or cell complex. In order to be able to stimulate two different portions of a cell or cell complex it is advantageous to use two ion channels or ion channel portions.

Normally, the spatial distribution of the ions will be determined by the ion passage surface area, when this is substantially smaller compared to the area of the interface between the ion-conductive channel and the electrode. On the other hand, the spatial distribution of the ions will normally be determined by the area of the interface between the ion-conductive channel and the electrode, when this is substantially smaller compared to the ion passage surface area.

Hence, neither a small interface area between the electrode and the ion-conductive channel, nor a small ion passage surface area, is necessary for reaching a more accurate spatial distribution of ions at a predetermined point of the electrolyte—but each of them, or both in combination, can be used to achieve it.

Although ion isolative means and encapsulation means are advantageous, these means are usually not necessary for the device to be able to transport ions.

According to one embodiment, the device further comprises an ion conductive waste channel and an waste electrode, which channel is ionically connected to said ion-conductive channel and to said waste electrode. The device further comprises means for limiting an electronic current between said source and said waste electrodes, such that at least after a voltage is applied across said waste channel a potential difference between said source and waste electrodes is maintained, which effects ion transport in the direction from said source electrode to said waste channel.

In other words, said waste channel is arranged to receive ions from said ion conductive channel. According to one embodiment, two waste channels are connected to the ion-conductive channel at a respective first and second portion of the channel. Each of the channels are connected to a respective waste electrode. A device comprising a waste electrode, preferably also comprises means for retaining a waste electrolyte in ionic contact with said waste electrode. The waste ion channel/electrode allows an improved temporal control of ion delivery, since the ion conductive channel may be partially or fully filled with the ion to be transported by transporting the ion to the waste electrolyte before the actual ion transport to the target electrolyte is initiated. Temporal control of the ion transport is of importance in many applications, e.g. applications involving studies of cell communication.

According to one embodiment, the device further compises at least one additional ion-conductive channel, spatially separated from said first ion-conductive channel, where the at least one additional ion-conductive channel is arranged to receive ions from said source electrode, arranged to release ions to said target electrode and to provide an additional ionic connection betweens said source and target electrodes. The device may also be provided with means for limiting an electronic current between said source and said target electrodes, such that at least after a voltage is applied across said additional channel a potential difference between said source and target electrodes is maintained, which effects ion transport from said source to said target electrode. The size of the ion passage surface area, and the interface between said additional electrode and said additional ion-conductive channel may have the corresoponding sizes as described above.

An embodiment where the ionic channel branches out in two separate ion channel portions is described below.

According to one embodiment, said ion conductive channel is arranged to branch out into at least a first and a second ion conductive channel portion which channel portions are spatially separated from each other. The device further comprises a second target electrode having a second ion passage surface, spatially separated from said first ion passage surface and arranged to be in ionic contact with an electrolyte; and means for limiting an electronic current between said source and said second target electrodes, such that at least after a voltage is applied across said second ion conductive channel portion a potential difference between said source and second target electrodes is maintained, which effects ion transport from said source to said second target electrode. Said first ion passage surface is arranged to transmit ions from said first channel portion, and said second ion passage surface is arranged to transmit ions from said second channel portion. Moreover, said means for retaining the electrolyte may be arranged for retaining the target electrolyte in ionic contact with said second ion passage surface. In other words, the target electrolyte covers both the first and second ion passage surface. According to a different embodiment, said first and second target electrodes are spatially separated from each other. Moreover the electrolyte covering said ion passage surface is spatially separated from the electrolyte covering said second ion passage surface. Hence, the electrolyte retaining means are preferably arranged such that a first and a second target electrolyte, which is to cover said first and second ion passage surface, respectively, are spatially separated from each other.

In other words, said second ion passage surface is arranged to be in ionic contact with an electrolyte, which is spatially separated from said target electrolyte. According to one example said first and second target electrodes forms a unitary element. According to a different example said first and second target electrodes are spatially separated from each other.

An embodiment where two separate ion channel portions are merged into a common ion-conductive channel is described below. This device comprises
at least one additional ion conductive channel,
at least one additional ion conductive source electrode, each comprising an ion passage surface,
means for retaining a source electrolyte in ionic contact with each of said at least one ion passage surface,
wherein a first portion of each of said at least one additional ion conductive channel is arranged in ionic contact with said first ion conductive channel, and
wherein a second portion of each of said at least one additional ion conductive channel is arranged in ionic contact with one of said at least one additional ion conductive source electrodes, respectively,
further comprising means for limiting an electronic current between said target electrode and each of said at least one additional source electrode, such that at least after a voltage is applied across a respective one of said at least one additional ion conductive channel, a potential difference between a source and a target electrode is maintained, which effects ion transport from said source to said target elecetrode. Moreover, said first ion conductive channel and said at least one additional ion conductive channel may further comprise a common point of intersection. Additionally, said first ion conductive channel and said at least one additional ion conductive channel may have a substantially equal angular distribution with respect to the spatial extension of the channel. Further, said first source electrode and at least one of said additional source electrode may form a unitary element. Said first source electrode and at least one of said additional source electrode may be spatially separated from each other.

According to one embodiment, the device comprises a first and a second channel portion which are merged into a common ion-conductive channel, which common ion-conductive channel branches out into a third and a fourth ion-conductive channel portions, such that ions may be transported from said first or second channel portion to either of said third or fourth channel portion, defined by the applied voltages.

Below a device comprising a pre-loading portion is described. According to one embodiment, said ion conductive channel further comprises an enlarged portion for storing ions, the enlarged portion is preferably arranged upstream of said target electrode, and downstream of a second portion of said at least one additional ion conductive channel and more preferably arranged downstream of each of said second portion of said at least one ion conductive channel. The pre-loading portion is a portion of an ion-conductive channel arranged to hold a predetermined amount of ions. This may for example be realized by a portion of the ion-conductive channel having an increased cross section area. The pre-loading region allows transport of a predetermined amount of ions without the need for measuring the amount of ions being transported when the transport is effected. This provides for devices that are easier to handle, cheaper to manufacture, and require less technical equipment during operation. A device may comprise one pre-loading portion or any number of pre-loading portions. If the device comprises more than one pre-loading portion, said pre-loading portions may be arranged in series or in parallel. If the device comprises more than one pre-loading portion, said pre-loading portions may have the same capacity for holding ions or different capacities for holding ions. Each pre-loading portion may be arranged to receive ions from more than one source electrolyte. Each pre-loading portion may be arranged to deliver ions to more than one source electrolyte. The pre-loading portion may preferably be combined with a waste electrode and a waste ion channel. The waste ion channel may preferably be connected to the pre-loading portion at the target electrode side of the pre-loading portion. The preloading portion may be combined with a flush electrode and a flush ion channel as described below. The flush ion channel may preferably be connected to the pre-loading portion at the source electrode side of the pre-loading portion.

Below a device comprising a flush channel is described.

According to one embodiment, said device further comprises a an ion conductive flush channel and a flush electrode, which channel is ionically connected to said ion-conductive channel and to said flush electrode up stream of said enlarged portion, and further comprising means for limiting an electronic current between said target and said flush electrode, such that at least after a voltage is applied across said flush channel a potential difference between said target and flush electrodes is maintained, which effects ion transport in the direction from said flush electrode to said target electrode.

The flush channel can be added to any of the device discussed above, but it is especially advantageous in combination with a waste electrode and/or pre-loading portion.

Below a device comprising a flush channel is described.

According to one embodiment, said device further comprises a an ion conductive flush channel and a flush electrode, which channel is ionically connected to said ion-conductive channel and to said flush electrode up stream of said enlarged portion, and further comprising means for limiting an electronic current between said target and said flush electrode, such that at least after a voltage is applied across said flush channel a potential difference between said target and flush electrodes is maintained, which effects ion transport in the direction from said flush electrode to said target electrode. The flush channel can be added to any of the device discussed above, but it is especially advantageous in combination with a wase electrode and/or pre-loading portion. The flush electrolyte may preferably comprise an electrolyte which will not affect any relevant processes in the target electrolyte. A flush electrolyte allows the ion-conductive channel to be flushed, e.g. when a source electrolyte is changed, to prevent an initial release of a previously transported ion when transport of a new ion is initiated.

According to one embodiment at least a portion of one of the ion conductive channels is curved or bent. Additionally, the electrolyte retaining means is preferably arranged to retain the electrolyte such that it covers said curve or bend.

Below a matrix configuration comprising 2 source electrodes and 2 target electrodes is described.

According to one embodiment the device additionally comprises:
- a first and a second additional ion conductive channels,
- an additional ion conductive source electrode, comprising an ion passage surface,
- an additional ion conductive target electrode, comprising an ion passage surface,
- means for retaining an additional source electrolyte in ionic contact with said ion passage surface of said additional source electrode,
- means for retaining an additional target electrolyte in ionic contact with said ion passage surface of said additional target electrode, wherein said first ion conductive channel is arranged in ionic contact with both said additional source electrode and said first target electrode, and
wherein said second ion conductive channel is arranged in ionic contact with both said first source electrode and said additional target electrode, further comprising means for limiting an electronic current between said first source electrode and each of said first and additional target electrodes and, for limiting an electronic current between said additional source electrode and each of said first and additional target electrode, such that at least after a voltage is applied across a respective one of said first and additional ion conductive channels a potential difference between a respective source and a target electrode is maintained, which effects ion transport from said source to said target electrode. According to one example the device further comprises a further ion-conductive channel arranged between said additional source and said additional target electrode, as well as means for limiting an electronic current between said additional source electrode and said additional target electrode, such that at least after a voltage is applied across a said further ion conductive channel a potential difference between said additional source and said additional target electrodes is maintained, which effects ion transport from said additional source to said additional target electrode.

Advantageously, two crossing ion-conductive channels are separated by ionically isolating means, preferably arranged as a layer or a sheet covering at least a portion of said ion-conductive channel. In other words, a device comprising a matrix arrangement as described above, wherein a portion of said first ion conductive channel is sandwiched between a substrate and one of the additional ion conductive channels, further comprises ion isolative means separating two crossing ion conductive channels from each other.

According to one embodiment, the source electrolyte is in physical contact with only one of the source electrodes. This is particularly advantageous for embodiments having at least two source electrodes, and where it is desirable to be able to separately control the ion transport from each of the electrodes. According to one example it is desired to transport ions from a common electrolyte first via a first source electrode and later via a second second electrode. If the electrolyte covers both a first and a second source electrode, the application of a potential to said first electrode, to effectuate the first ion transport, creates a field in the electrolyte, due to the potential difference between the electrodes. Hence, the application of a potential to said first electrode might effectuate an ion transport also via said second electrode. This may be avoided by separating the electrolyte which is in contact with the first electrode, from the electrolyte which is in contact with said second electrolyte.

According to one embodiment the length of the ion conductive channel is with the range of about 5 μm and 3 dm, or shorter than 1 mm.

The thickness of the ion-conductive channel or the electrodes is normally 10 nm to 1 mm, or 100 nm to 100 μm.

The substrate, the electrodes, the ion-conductive channel, the isolative means and/or the electrolyte retaining means may be arranged as layers.

According to one embodiment the ion channel and or the electrodes is arranged of electrochemically active material. This is not necessary for the ability of the device to transport ions. The ability of the ion channel to maintain a voltage difference suffice. According to one embodiment at least one of the electrodes is arranged of an electrically and ionically conducting polymer material. This is advantageous as it normally is bio compatible, and thus suitable for use adjacent to cell and cell complex.

According to one embodiment the ion conductive channel and at least one of the electrodes are formed of the same material. This is advantageous as it facilitates the manufacturing of the device, as the complexity of the device is substantially reduced.

According to one embodiment, the materials in physical or ionic contact with the electrolyte is non-metallic. This is advantageous, as a release of metallic ions into the electrolyte may harm cells contained therein. In other words, the electrode is preferably non-metallic.

Further, for a device comprising at least two separate ion-conductive channels, or ion-conductive channel portions it may be advantageous to adapt the impedance of the channels, with respect to each other and/or with respect to the ions which are to be transported. The impedance may be altered by varying cross section and/or the volume of the ion conductive channel. According to one example the cross-section of the ion-conductive channel gradually decreases along the length of the channel. According to another example the ion conductive channel comprises a first portion having a first cross-sectional area and a second portion having a second cross-sectional area, wherein said first cross-section area is preferably at least twice as large as said second cross-sectional area, preferably three times larger and most preferably four times larger than said second cross-sectional area. According to another example the variation of the cross-sectional area of the ion-conductive channel is less than 10%, or less than 5% along the length of the channel. According to one embodiment the channel is band shaped.

Below is described an embodiment by which ions may first be transported from a first source to a first target electrolyte, and thereafter from said first target to a second target electrolyte. This may be achieved by connecting two of the above described devices are connected in series.

According to one aspect of the invention an arrangement for electrically controlled transport of ions is provided which comprises:
a first device arranged as described above;
a second device arranged as described above;
which devices are arranged in series with each other, wherein the target electrolyte of said first device and the source electrolyte of said second device are one and the same,
such that ions may be transported from the source electrolyte of said first device via the common electrolyte to the target electrolyte of said second device,
at least after a first potential difference has been applied across the ion-conductive channel of said first device and a second potential difference has been applied to the ion-conductive channel of the second device.

According to one embodiment, the potential difference between said first and second potential is substantially equal to the potential difference between said third and fourth potential. Further, the potential difference between said second and third potentials is preferably substantially smaller, compared to the potential difference between said first and second potential; and said third and fourth potential, respectively.

According to one embodiment the second and third potential, respectively, is within the range of between said first potential to said fourth potential.

According to one embodiment elements for the device may comprise a combination of features selected from a group comprising: waste channels; pre-loading portions; flush channels and matrix configurations. In other words, at least one of the ion-conductive channels of a device arranged in e.g. a matrix configuration as described above; may further be provided with e.g. a waste electrode and a pre-loading region.

According to one embodiment, a method of operating a device as described above, comprises the steps of:
a) providing a source electrolyte comprising the ions to be transported,
b) providing a target electrolyte comprising at least one cell,
c) bringing the source electrode of the device in physical contact with the source electrolyte, and bringing the target electrode of the device in physical contact with the target electrolyte such that said at least one cell is arranged adjacent to, or in direct physical contact with, an ion passage surface of said target electrode,
d) applying a voltage across the ion-conductive channel of the device, effecting ion transport from the source electrolyte to the target electrolyte.

According to one embodiment, a method of operating a device as described above, comprises the steps of:
a) providing a source electrolyte comprising at least one cell,
b) providing a target electrolyte,
c) bringing the source electrode of the device in contact with the source electrolyte such that said at least one cell is arranged adjacent to, or in direct physical contact with, an ion passage surface of said target electrode, and bringing the target electrode of the device in contact with the target electrolyte,
d) applying a voltage across the ion-conductive channel of the device, effecting ion transport from the source electrolyte to the target electrolyte.

According to one embodiment, a method of operating a device as described above, comprises the steps of:
a) providing source electrolyte comprising the ions to be transported,
b) providing a target electrolyte,
c) providing a waste electrolyte,
d) bringing the source electrode of the device in contact with the source electrolyte, bringing the target electrode of the device in contact with the target electrolyte, and bringing the waste electrode of the device in contact with the waste electrolyte,
e) applying a first voltage between the source and waste electrodes, effecting ion transport from the source electrolyte to the waste electrolyte,
f) applying a second voltage between the source and target electrodes, effecting ion transport from the source electrolyte to the target electrolyte.

According to one embodiment, a method of operating a device as described above, comprises the steps of:
a) providing source electrolyte comprising the ions to be transported,
b) providing a target electrolyte,
c) providing a waste electrolyte,
d) providing a flush electrolyte,
e) bringing the source electrode of the device in contact with the source electrolyte, bringing the target electrode of the device in contact with the target electrolyte, bringing the waste electrode of the device in contact with the waste electrolyte, and bringing the flush electrode of the device in contact with the flush electrolyte,
f) applying a first voltage between the source and waste electrodes, effecting ion transport from the source electrolyte to the waste electrolyte via the pre-loading region,
g) applying a second voltage between the flush and target electrodes, effecting ion transport from the flush electrolyte to the target electrolyte and transport of the ions present in the pre-loading region to the target electrolyte.

Thus, the invention involves limiting an electronic current, i.e. a current or flow of electrons, in a material, while maintaining the ion conductivity of the material. A limitation of the electronic current in the material can e.g. be achieved by limiting the electron conductivity. This limitation makes it possible to maintain a potential difference over the material when a voltage is applied across it. The potential difference can then be used as a driving force for ion transport from one portion of the material to another.

Thus, by the present invention is provided a device or the use of a device by which ions are transported to prokaryotic or eukaryotic cells, including tissue, cultivated or otherwise present on the target electrode or in the target electrolyte. By means of direct or indirect action, transported ions may affect said cells and induce biological processes therein. Accordingly, the present invention is useful in cell communication research, wherein said apparatus or device can be utilized for delivering ions to cells in order to allow evaluation of the response of said cells.

In an embodiment, the device may be used for stimulating a single cell using several different ionic stimuli simultaneously or consecutively. In another embodiment, the device may be used for stimulating a single cell with a spatial resolution which allows different portions of said single cell to be stimulated by different ionic stimuli.

The device may also be used to transport ions in the opposite direction, i.e. from a cell, e.g. in order to analyze ionic species that are excreted from a cell under certain conditions. In other words, the inventive device may be used as a means for delivery of ions to cells, as well as a part of an arrangement for analyzing cellular response.

Ions:

The term "ion" as used herein encompasses not only positively or negatively charged monovalent or multivalent ionic species of atomic elements, but also other molecular species carrying a net positive or negative charge. Hence, in an embodiment of the invention it is intended to transport charged biologically active molecules or macromolecules such as charged amino acids, DNA, DNA sequences/fragments or plasmids, proteins, vitamins, peptides or hormones. In one embodiment of the invention, the ions that may be transported are cations, for example metal ions, such as potassium or calcium ions. In another embodiment of the invention the ions that may be transported are anions. The transported "ions" may act as stimuli for the cells. These stimuli may turn on a cellular process or turn off a cellular process, or act as an inhibitor. A non-limiting example is potassium which may act as stimuli for neuronal cells by opening the voltage-operated Ca2+ channels in the cell membrane. A non-limiting example of an inhibitor may be cadmium which may block the voltage-operated Ca2+ channels in the cell membrane. The term ion also encompasses species that may be charged by setting a certain pH of the electrolyte solution or channel. The pH needed to charge these species may be calculated from the pKa of these molecules. The term ion also encompasses molecules which may be chemically modified to obtain a net charge, e.g. by attaching an ion to them.

The term ion may also encompass aggregate particles carrying a net charge, e.g. by emulsion of a given molecule by a surfactant species, either of which may carry charge. In addition, the cladding may comprise charged and uncharged species such that the net aggregate charge may be tailored. Examples of such cladding materials include fatty acids, dodecylbenzene sulfonate, lecithin, and cetearyl alcohol.

Ionic Contact:

A first and a second material are in ionic contact when a substantial amount of ions comprised in the first material can move from the first material to the second material, possibly via a third material. The ionic movement may be caused by diffusion or by an applied electric field.

A material which provides an ionic connection between a first and a second material, is a material which is ionically conductive and in ionic contact with both said first and said second material.

Directly or Indirectly Attached:

Two parts which are directly attached to each other are in direct physical contact with each other. With respect to this invention, when a first part is directly attached to a second part, which second part is directly attached to a third part, said first and third parts are referred to as being indirectly attached to each other. Similarly, when said third part is directly attached to a fourth part, said first and fourth parts are referred to as being indirectly attached to each other.

Semi-Solid Material:

The term semi-solid material refers to a material, which at the temperatures at which it is used has a rigidity and viscosity intermediate between a solid and a liquid. Thus, the material is sufficiently rigid such that it does not flow or leak. Further, particles/flakes in the bulk thereof are substantially immobilized by the high viscosity/rigidity of the material.

In a preferred case, a semi-solid material has the proper rheological properties to allow for the ready application of it on a support as an integral sheet or in a pattern, for example by conventional printing methods. After deposition, the formulation of the material should preferably solidify upon evaporation of solvent or because of a chemical cross-linking reaction, brought about by additional chemical reagents or by physical effect, such as irradiation by ultraviolet, infrared or microwave radiation, cooling etc.

The semi-solid or solidified material preferably comprises an aqueous or organic solvent-containing gel, such as gelatin or a polymeric gel.

Electrochemically Active Material:

With respect to this invention the term electrochemically active material refers to a material which may comprise a proportion of a component in an electrochemical reaction when it is in contact with an electrolyte and a voltage is maintained across it. Examples of such electrochemically active materials include electrically conductive polymers, as will be described below, carbon and certain metal oxides, such as indium tin oxide (ITO), nickel oxide (NiO), manganese dioxide (MnO2) and tungsten oxide (WO3).

Electrolyte:

The electrolyte for use with the device or method of the present invention should preferably be based on a solvent which permits ionic conduction in the electrolyte, i.e. which allows for the dissociation of ionic substances such as salts, acids, bases etc. The solvent and/or the ionic substance may contribute nucleophiles. Possible electrolytes for use in combination with the inventive device are solutions of salts, acids, bases, or other ion-releasing agents in solvents that support the dissociation of ionic species, thus allowing ionic conductivity. In applications where it is required, the electrolytes may comprise buffer solutions, such as buffer solutions suitable for use with living organisms or biomolecules, such as proteins. Examples of such buffers include $NaHPO_4$ and sodium acetate. As other non-limiting examples of possible electrolytes, mention can be made of: aqueous solutions of potassium acetate, calcium acetate, NaCl, $Na_2SO_4$, HCl, $H_3PO_4$, $H_2SO_4$, KCl, $RbNO_3$, $NH_4OH$, CsOH, NaOH, KOH, $H_2O_2$; Ringer's solution, organic solvents such as acetonitrile, pyridine, DMSO, DMF, dichloromethane, etc., in combination with suitable salts, such as lithiumperchlorate and tertiary ammonium salts, e.g. tetra-butyl ammonium chloride; inorganic solvents such as hypercritical $CO_2$, liquid $SO_2$, liquid $NH_3$, etc., in combination with salts that dissociate in these solvents; solvents displaying auto-dissociation, which results in the formation of ionic species, such as water, formic acid and acetic acid. The term electrolyte also encompasses solutions comprising charged biologically active molecules or macromolecules such as charged amino acids, DNA, DNA fragments and plasmids, proteins, vitamins, peptides or hormones. An electrolyte may also comprise cell culturing media or ingredients thereof, such as proteins, amino acids, vitamins, and growth factors.

The term electrolyte may also encompass solutions comprising charged aggregate particles such as emulsified species, or species clad with some additional charged species.

The electrolyte may also be in a semi-solid or solidified form, preferably comprising an aqueous or organic solvent-containing gel as described above. However, solid polymeric electrolytes are also contemplated and fall within the scope of the present invention. Furthermore, the term electrolytes also encompasses liquid electrolyte solutions soaked into, or in any other way hosted by, an appropriate matrix material, such as a paper, a fabric or a porous polymer.

It also includes so called ionic liquids, which is liquids that contains essentially only ions. Examples of these are quarterial ammonium salts, phosphonium salts, mixtures of 1,3-dialkylimidazolium or 1-alkylpyridinium halides and trihalogenoaluminates, EMIM EtOSO$_3$ (1-Ethyl-3-methylimidazolium ethylsulfate), LiClO4 dissolved in 1-butyl-3-methylimidazolium tetrafluoroborate [bmim] [BF$_4$].

Cell Culture Area:

With cell culture area is meant the area of the ion pump device onto which cells are intended to culture/grow. The cell culture area may be the complete surface under the target or source electrolyte. In some cases, for instance when using expensive stem cells, it may be an option/requirement to reduce the cell culture area to a surface area that is smaller than the electrolyte area. This may for instance be achieved by adding a barrier (like a fence) or patterning adhesion molecules in order to confine the cells to a certain area. The cell culture area comprises typically the target or source electrode area that is covered by the electrolyte. However, in some designs/embodiments the cell culture area comprises other surfaces of the ion pump, such as the support surface 107, the insulating layer surface 108, or 108c, or the electrical contact portion surface 121 (See for instance FIG. 1h)

Electrodes:

The source and target electrodes of the inventive device each comprises an electrochemically active material. In a preferable configuration the electrodes comprise a material or a combination of materials which are capable of conducting both ions and electrons. In a more preferable configuration the molecular structure of the electrode allows for ions of at least a low molecular weight to enter the electrode via an electrolyte in ionic contact with the material, and for these ions to move within the material with some degree of freedom.

Ion conductivity and electron conductivity may be provided by the same material. Examples of materials which are able to conduct both ions and electrons are some electrically conductive polymers as will be described in greater detail below. An advantage of conducting polymers may be that no harmful reaction products are created in the redox reactions.

It is also possible to use a combination of two or more materials where at least one of the materials is electronically conductive and at least one of the materials is capable of conducting ions. Examples of such combinations, which may be used in a device according to the present invention, include an electronically conductive material, such as indium tin oxide, and an ion-conductive hydrogel.

The electrodes may also comprise further organic or inorganic materials, which are capable of conducting ions but not capable of conducting electrons, which materials are included in order to facilitate ion transport into and within the electrodes. Non-limiting examples of such materials are polymer materials, such as hydrogels and polyelectrolytes. Such additional electrode materials may be either dispersed in, or be arranged as a separate layer in contact with, an electronically conductive electrode material.

The electrodes of the inventive device preferably comprise an electrochemically active material. Preferably, said electrode material is an organic material. More preferably said organic material is a polymer, and may be an electrically conductive polymer. Electrically conductive polymers suitable for use in the device of the invention, are preferably selected from the group consisting of polythiophenes, polypyrroles, polyanilines, polyisothianaphthalenes, polyphenylene vinylenes and copolymers thereof such as described by J C Gustafsson et al. in Solid State Ionics, 69, 145-152 (1994); Handbook of Oligo- and Polythiophenes, Ch 10.8, Ed D Fichou, Wiley-VCH, Weinhem (1999); by P Schottland et al. in Macromolecules, 33, 7051-7061 (2000); by M Onoda in Journal of the Electrochemical Society, 141, 338-341 (1994); by M Chandrasekar in Conducting Polymers, Fundamentals and Applications, a Practical Approach, Kluwer Academic Publishers, Boston (1999); and by A J Epstein et al. in Macromol Chem, Macromol Symp, 51, 217-234 (1991). In one especially preferred embodiment, the electrically conductive polymer is a polymer or copolymer of a 3,4-dialkoxythiophene, in which said two alkoxy groups may be the same or different or together represent an optionally substituted oxy-alkylene-oxy bridge. It is particularly preferred that the polymer is a polymer or copolymer of a 3,4-dialkoxythiophene selected from the group consisting of poly(3,4-methyleneioxythiophene), poly(3,4-methylenedioxythiophene) derivatives, poly(3,4-ethylenedioxythiophene), poly(3,4-ethylenedioxythiophene) derivatives, poly(3,4-propylenedioxythiophene), poly(3,4-propylenedioxythiophene) derivatives, poly(3,4-butylenedioxythiophene), poly(3,4-butylenedioxythiophene) derivatives, and copolymers therewith.

In one embodiment of the device, said electrically conductive polymer is poly(3,4-ethylenedioxythiophene) (PEDOT). Preferably the electrodes further comprise a polyelectrolyte compound, more preferably said polyelectrolyte compound is poly(styrene sulfonic acid) or a salt thereof. One especially preferred material for use in the electrodes of the device of the invention is poly(3,4-ethylenedioxythiophene) with a poly (styrene sulfonate) polyanion (in the following referred to as PEDOT:PSS). In an embodiment the electrodes are present in the form of a thin layer of PEDOT:PSS deposited on a solid substrate.

The electrodes of the inventive device may further comprise a hydrogel. The hydrogel is preferably based on polymers selected from the group consisting of polyacrylates, such as poly(2-hydroxyethyl methacrylate) and poly(acrylamide), polyelectrolytes, such as poly(styrene sulfonic acid) (PSS) and poly(acrylic acid) (PAA), polysaccharides, such as agarose, chitosan and dextran, gelatin, polyvinyl alcohol, polyvinyl pyrrolidone, polyethylene oxide and polyethylene glycol.

In an embodiment the electrodes are present in the form of a thin layer of PEDOT:PSS deposited on a solid substrate and a thin layer of chitosan deposited on said PEDOT:PSS layer. Other combinations of materials can also be used.

The electrodes are preferably arranged in a common plane on a solid substrate. Preferably the electrodes are deposited onto said substrate by printing or lamination techniques. Use of printing methods in combination with conventional semiconductor processing methods, such as lithography and etching, allows for the electrodes to be patterned with a resolution of about 1 μm. This allows the inventive device to be manufactured in miniature scale, which e.g. is useful in biochemical and cell applications where samples and preparations may be available only in very minute amounts. Preferably the thickness of the electrodes is less than 1 mm. The thickness is measured in a direction normal to the support on which the electrode is arranged.

An embodiment of the device is provided, in which at least one of the electrodes is biocompatible. The term biocompatible is used herein to characterize a material or a surface allowing cultivation of cells thereon or in close association therewith. Cultivation of cells refers to attachment, maintenance, growth and/or proliferation of said cells. An example of an electrode material according to the invention that provides a biocompatible surface is PEDOT:PSS. The biocompatibility of an electrode allow for studies of cellular activities in cells cultivated on or in close association with the electrode.

Ion-Conductive Channel (Ion Channel):

The ion-conductive channel used in the invention is made of a solid or semi-solid material which is able to conduct ions. According to one embodiment of the invention the ion-conductive channel is essentially electronically non-conductive, i.e. the capability of conducting electrons is substantially limited. When reference is made to the ion-conductive channel being or being rendered "essentially non-conductive" or simply "non-conductive", those terms are intended to encompass completely insulating materials as well as materials which has been rendered sufficiently deactivated and insulating to be useful e.g. as an electrically insulating barrier between areas of the polymer that have not been rendered essentially non-conductive. Such essentially non-conductive polymers have preferably had their conductivity reduced by a factor greater than $10^2$, and even more preferably greater than $10^5$. Thus, to render a polymer essentially non-conductive or to render a polymer non-conductive is, for the purpose of the present invention, to be interpreted as the action of substantially reducing the conductivity of the polymer.

When a voltage is applied across an ion-conductive channel that has a limited electron conductivity, a potential difference between anode and cathode will be maintained. The potential difference generated will affect transport of ions present in the ion-conductive channel or in the ion-conductive electrodes connected to the ion-conductive channel. The mechanism behind the ion transport has not been fully elucidated. It should be pointed out, however, that the present invention does not depend on any particular theoretical explanation. Neither does the skilled person need to rely on any particular theoretical foundation in order to carry out the invention. One driving force for ion transport between the two electrodes is electrochemical reactions in an electrochemically active electrode material, which are effected when a voltage is applied to such a material in contact with an electrolyte. When a conductive polymer, such as PEDOT:PSS, is used as the electrode material and a voltage is applied across the ion-conductive channel the region of the source electrode, which is in contact with the source electrolyte, will be oxidized, and the region of the target electrode, which is in contact with the target electrolyte, will be reduced according to the reaction below.

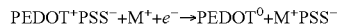

$PEDOT^+PSS^- + M^+ + e^- \rightarrow PEDOT^0 + M^+PSS^-$

Another driving force for the ion transport is the force imposed on any charged entity present in the electrical field which is created in the ion-conductive channel when a voltage is applied across the channel.

The capability of the ion-conductive channel of being ion-conductive, whilst being essentially electronically non-conductive, may be inherent in the material used. Some materials that could be used as ion-conductors in the ion-conductive channel of the inventive device include polyelectrolytes such as poly(styrene sulfonic acid) (PSS) and poly(acrylic acid) or hydrogels based on polyacrylates, such as poly(2-hydroxyethyl methacrylate) and poly(acrylamide), polyelectrolytes, such as poly(styrene sulfonic acid) (PSS) and poly(acrylic acid) (PAA) and derivatives thereof, polysaccharides and derivatives thereof, such as agarose and dextran, protein based gels such as gelatin and other water soluble polymers, such as polyvinyl alcohol, polyethylene oxide, polyvinyl pyrrolidone, polyethylene glycol and chitosan. Ionic liquids in a semi-solid state could also be used. Other examples of materials which are inherently ion-conductive and essentially electronically non-conductive include conductive polymers such as those mentioned above, which have been overoxidized and thereby rendered electronically non-conductive. In context of this invention an overoxidized state is a non-reversible electronically non-conducting state of the material.

In some embodiments, the material used in the ion-conductive channel may be the same as a material used to facilitate ion transport in the electrodes. For example, the ion-conductive channel may comprise a hydrogel in order to facilitate ion transport.

Preferably the ion-conductive channel comprises an organic material, more preferably said organic material comprises a polymer. The polymer may preferably be a hydrogel based on a polymer selected from the group consisting of polyacrylates, such as poly(2-hydroxyethyl methacrylate) and poly(acrylamide), polyelectrolytes, such as poly(styrene sulfonic acid) (PSS) and poly(acrylic acid) (PAA) and derivatives thereof, polysaccharides and derivatives thereof, such as agarose and dextran, protein based gels such as gelatin and other watersoluble polymers, such as polyvinyl alcohol, polyethylene oxide, polyvinyl pyrrolidone and polyethylene glycol. The ion-conductive channel may also comprise a polyelectrolyte, such as for example polystyrene sulfonic acid) (PSS) or poly(acrylic acid). In an embodiment of the device according to the invention, the ion-conductive channel comprises an over-oxidized electrically conductive polymer material, preferably over-oxidized poly(3,4-ethylenedioxythiophene):poly(styrene sulfonic acid) (PEDOT:PSS).

In a preferred embodiment of the invention, the ion-conductive channel, which is used to ionically connect the source and target electrodes, comprises the same conductive polymer as that present in said electrodes, with the difference that the conductive polymer present in the ion-conductive channel has been overoxidized, i.e. its electron conductivity has been permanently reduced by means of oxidation.

In another embodiment of the device, said source and target electrodes are two regions of a single conductive polymer layer, separated by a region of said layer which has been overoxidized. In other words, said electrodes and said ion-conductive channel is formed of the same material and arranged as a unitary element.

In a preferred embodiment, the device of the invention is all-organic, i.e. all materials present in the device are organic. One advantage of all-organic devices is that they may be more readily recycled than devices comprising a combination of organic and inorganic materials that may require disassembly prior to recycling.

An inherent advantage of a device according to the invention is the low voltage required to effect ion transport from a source to a target electrolyte.

Magnitude and polarity of the voltages to be applied in the inventive device and method will vary depending on a number of factors, such as choice of electrode material(s), the ion to be transported, the distance over which the ions are transported, etc. The polarity of the applied voltages will easily be selected by a person skilled in the art, taking into account the type of charge (positive or negative) of the ion to be transported. The magnitude of the voltage to be applied may in the light of the present invention easily be determined in order to transport a desired amount of ions.

The voltage applied across the ion conductive channel may for example be within the range of from about 0.01V to about 100 V. The optimal voltage to apply between electrodes will depend on the characteristics of the polymer used, the electrolyte used, the ion to be transported and the manner in which the voltage is applied to the interface between polymer and electrolyte. However, the voltage is preferably in the range of from 0.01 to 100 V, more preferably in the range of from 0.01 V to 20 V.a Cells:

As used in the present disclosure, the term cells is meant to encompass all types of animal or plant cells that may be of interest to cell interaction studies. Non limiting examples of types of cells that may be used with the present disclosure include eukaryotic cells which are cells with nucleus and prokaryotes which are cells without nucleus. Non limiting examples of eukaryotic cells include stem cells and other nerve cells, cells from the immune system, epithelial cells, and endothelial cells. Non limiting examples of prokaryotic cells include different kinds of bacteria. A person skilled in the art of cellular research would readily be able to name any number of different cells that may be used with the present disclosure.

Cell sizes of cells useful with the present invention are typically in the range of 1 μm-1 mm and may for example be in the range of 10-500 μm in diameter or in the range of 10-100 μm or 10-50 μm. Also some types of cells that may be of interest will be straggling.

With a cluster of cells, as the term is used in the present disclosure, is meant a number of adjacent cells ranging from 2 cells to millions of cells. Typically a cluster of cells may comprise about 2-1 000 000 cells, for example about 100 000-1 000 000 cells. One specific example of a cluster of cells would comprise a slice or a small portion of a slice of tissue from an organ or neurons that would be of interest to study using a device according to the prsent disclosure. A person skilled in the art of cellular research would readily be able to name other types of cell clusters that may be of interest to study using a device according to the prsent disclosure.

Insulation Material:

In the ion pump devices reference is made to an insulation material. These materials may be either electrically insulating, ionically insulating or both electrically and ionically insulating at the same time. A non-limiting example is the insulation 108c in FIG. 1h which has to be ionically insulating to prevent leakage of ions from the channel 103. The insulation material may or may not be photopatternable. They encompass/comprise polymers such as photo resists including SU-8, polyimide, different kinds of lacquer such as acrylic resin, evaporation of oxides such as $SiO_2$, or nitrides such as $Si_3N_4$, spin on glass, ceramics, lamination foils.

Encapsulation Material:

In the present disclosure, reference is made to an encapsulation material. This material may be either electrically insulating, ionically insulating or both electrically and ionically insulating at the same time. The encapsulation material may or may not be photopatternable. They encompass/comprise polymers such as photo resists including SU-8, polyimide, different kinds of lacquer such as acrylic resin, evaporation of oxides such as $SiO_2$, or nitrides such as $Si_3N_4$, spin on glass, ceramics, lamination foils.

Substrate:

The substrate onto which the ion pump may be fabricated preferably is electrically and ionically insulating and may comprise rigid materials such as Si wafers with an insulating oxide (SiOx) or nitride layer ($Si_3N_4$), glass wafers such as pyrex wafers, glass substrates, such as microscope slides, plastic substrates such as PET, polystyrene, used in petridishes, and ceramics. The substrates may also be flexible such as plastic films, Orgacon films (both plastic and paper), or paper based materials.

Manufacturing:

The ion transport device according to the invention is also particularly advantageous in that it can be easily realized on a support, such as polymer film or paper. Thus, the different components can be deposited on the support by means of conventional printing techniques such as screen printing, off-set printing, gravure printing, ink-jet printing and flexographic printing, or coating techniques such as knife coating, doctor blade coating, extrusion coating and curtain coating, such as described in "Modern Coating and Drying Technology" (1992), eds E D Cohen and E B Gutoff, VCH Publishers Inc, New York, N.Y., USA. In the embodiments of the invention that utilize a conductive polymer material in the electrodes and/or ion-conductive channel (ion channel), this material can also be deposited through in situ polymerization by methods such as electropolymerization, UV-polymerization, thermal polymerization and chemical polymerization. As an alternative to these additive techniques for patterning of the components, it is also possible to use subtractive techniques, such as local destruction of material through chemical or gas etching, by mechanical means such as scratching, scoring, scraping or milling, or by any other subtractive methods known in the art. An aspect of the invention provides such processes for the manufacture of an ion transport device from the materials specified herein.

Thus, in one embodiment of the device, said electrodes and said ion-conductive channel (ion channel) are directly or indirectly attached to a solid support such as glass or to a flexible support such as polymer film or paper.

The ion transport device according to the invention may preferably be encapsulated, in part or entirely, for protection of the device. The encapsulation retains any solvent needed for e.g. the liquid or solidified electrolyte to function, and also keeps oxygen from disturbing the electrochemical reactions in the device. Encapsulation can be achieved through liquid phase processes. Thus, a liquid phase polymer or organic monomer can be deposited on the device using methods such as spray-coating, dip-coating or any of the conventional printing techniques listed above. After deposition, the encapsulant can be hardened for example by ultraviolet or infrared irradiation, by solvent evaporation, by cooling or through the use of a two-component system, such as an epoxy glue, where the components are mixed together directly prior to deposition. Alternatively, the encapsulation is achieved through lamination of a solid film onto the ion transport device. In preferred embodiments of the invention, in which the components of the ion transport device are arranged on a support, this support can function as the bottom encapsulant. In this case encapsulation is made more convenient in that only the top of the sheet needs to be covered with liquid phase encapsulant or laminated with solid film.

The inventive device may also be manufactured using conventional semiconductor processes, such as photolitography and etching. When such methods are used, the electrode material(s) may preferably be deposited onto the substrate using any suitable deposition method, e.g. printing or lamination. The substrate carrying the electrode material(s) may then be patterned using conventional photoresist/etching techniques, e.g. as described in greater detail in Preparatory Example 1. An ion-conductive channel (ion channel) can be obtained e.g. by deposition of a suitable ion-conductive, electronically non-conductive material or otherwise as defined above.

Further Embodiments

The device according to the invention may also present further features, which facilitate use of the device. Such features include for example terminals for connecting a voltage source to the electrodes of the device, means for encapsulating the device in order to make it more robust to handling, and to prevent evaporation or contamination of liquid electrolytes.

When the device is used, a first liquid or solidified electrolyte can advantageously be deposited so that it covers, at least partly, the source electrode, and a second liquid or solidified electrolyte can advantageously be deposited so that it covers, at least partly, the target electrode.

In one embodiment, the electrodes of the device are arranged such that solid or liquid electrolytes may be deposited directly onto the desired electrodes.

Another embodiment of the inventive device further comprises means for retaining a source and target electrolyte on the device, arranged such that the electrolytes are in contact with the desired electrodes. In an embodiment the device comprises means for retaining one of said source and target electrolytes. In another embodiment the device further comprises means for retaining the other of said source and target electrolytes on the device.

In some embodiments the electrolytes may be confined to a certain area of the device by means of one or more physical or chemical confinement methods. The electrolytes may for example be confined by walls or the like arranged on the device surface, by openings in a partial encapsulation of the device as described herein, or by suitable chemical or physical treatment of the device surface, such as rendering the surface partially hydrophobic, e.g. using a fluorinated coating.

In an embodiment, the source and target electrolytes may be retained on the device by means of a container, arranged such that the electrolytes are in contact with the desired electrode(s). Said container may preferably be made of glass or a polymer material, but other materials may also be used. The container may be open or partly or fully sealed.

Said means or container for retaining electrolytes on the device are preferably arranged such that said source electrolyte and said target electrolyte are held separate from each other. The surface of said container is preferably biocompatible.

The device according to the invention may further comprise means for measuring the amount of ions being transported from the source to the target electrode by measuring the current between the source and the target or the target and the target resetting or the source and the source resetting electrode.

In an embodiment of the invention, wherein e.g. protons are transported, the ion transport results in a pH-change in the target electrolyte.

A device according to the invention may be arranged to deliver ions from one electrolyte containing the ion to be transported to more than one receiving electrolyte. This is achieved by patterning the electrodes and ion-conductive channel(s) in different ways and arranging the electrolytes on the patterned electrodes in such a way that ion transport can be achieved between different electrolytes depending on across which electrodes a potential is applied. Such a multiple receiving electrolyte arrangement allows electrically controlled transport of ions from one source electrolyte to more than one receiving electrolyte. Ion transport to the different receiving electrolytes may be performed in parallel or in sequence, and each receiving electrolyte may be addressed individually through individually applied voltages.

In a similar manner a device according to the invention may be arranged to deliver ions from more than one electrolyte containing an ion to be transported to one receiving electrolyte. Such a multiple source arrangement allows electrically controlled transport of different amounts of different ions to one receiving electrolyte. For example, when $Ca^{2+}$ and $K^+$ are present in two different source electrolytes, their time-resolved arrival at the target electrolyte may be controlled by operating subsequently the ion-conductive channels arranged for transport from the respective source electrolytes. As an alternative, a source electrolyte may comprise different ions such that different ions may be transported from one source electrolyte to a target electrolyte. These arrangements allow for a time-resolved transport of different ions. For example, when $Ca^{2+}$ and $K^+$ are present in the same source electrolyte, their time-resolved arrival at the target electrolyte may be controlled by the voltage applied across the ion-conductive channel.

The device of the present invention may be used to create ion concentration gradients close to the target electrode. Such ion concentration gradients may e.g. be useful in bioanalytical applications, such as cell signalling studies.

The device of the present invention may be used to create oscillating ion concentrations close to the target electrode. Such oscillating ion concentration gradients mimic natural processes, and may e.g. be useful in bioanalytical applications.

The device of the present invention will be useful in cell communication studies, wherein a cell may for example be stimulated by ions transported to the cell using the device and a cellular response may be studied or used by transporting secreted ions from a cell using the device.

A cell contact site may be realized by means of one or more physical or chemical confinement methods. The cell(s) may for example be confined by walls or the like arranged on the device surface, by openings in a partial encapsulation of the device as described herein, or by suitable chemical or physical treatment of the device surface.

In an embodiment, the cell(s) may be retained on the device by means of a container, arranged such that the cell(s) are in contact with the desired electrodes. Said container may preferably be made of glass or a polymer material, but other materials may also be used. The container may be open or partly or fully sealed. In an embodiment of the invention, said apparatus comprises a multiplicity of said devices and their related cell contact sites, the devices and their related cell contact sites preferably being arranged to create a matrix system thereof, wherein each device may be addressed individually for ion transport purposes. An example of an application where such a matrix system would be useful is in microwell plates, as used e.g. for cell culturing and biochemical research. Management of such a matrix system could conveniently be handled by a personal computer.

In an embodiment of the inventive apparatus, each device and its related cell contact site is arranged to provide ionic contact between a single cell and the target or source electrolyte, respectively. Such single cell contact is rendered possible by the small dimensions achievable in the production of the inventive device, cf. above. Thus, according to the present invention it is possible to address a single cell, or even specific portions of a single cell to, or from, which ions are being transported. Such spatially resolved ion transport has not been possible using any prior art technique.

In an embodiment of the inventive apparatus, said ionic contact between the cell and the target or source electrolyte is provided through a disruption in an insulating layer arranged between the cell and the device. Such a disruption would allow for the provision of contact with a selected cell or group of cells only, whereas the insulating layer would inhibit contact with ambient cells in a cell culture or tissue. In turn, the insulating layer may be coated with a biocompatible material so as to facilitate cell cultivation thereon.

In summary, the inventive device can be employed to deliver ions to single cells or cell populations in order to study, regulate and control different aspects of cell signalling, e.g. when cells are subjected to elevated concentrations of a certain ion(s). It should be pointed out that the different opportunities presented for transporting ions to or from a selected group of cells, or even a single cell, provides a major advantage to such applications.

Another advantage of an apparatus or a device according to the present invention is that it can be manufactured using e.g. conventional printing techniques. This allows for development of affordable single-use articles comprising the inventive device or apparatus, e.g. for use in cell communications research or in clinical settings.

Different arrangements of a cell, whether derived from a cell culture, a tissue or elsewhere, in relation to the device are possible while still providing the desired ion transport function. Thus, in one embodiment, said cell is present in the target or source electrolyte, respectively. In such embodiment, the target or source electrolyte, respectively, may comprise cell culture medium if desirable for the maintenance or growth of said cells. It is also possible that the cell is present on said target or source electrode, respectively. A biocompatible electrode may, e.g., be suitable as a support for cultivation of cells.

A BRIEF DESCRIPTION OF THE DRAWINGS

Figure 11A:
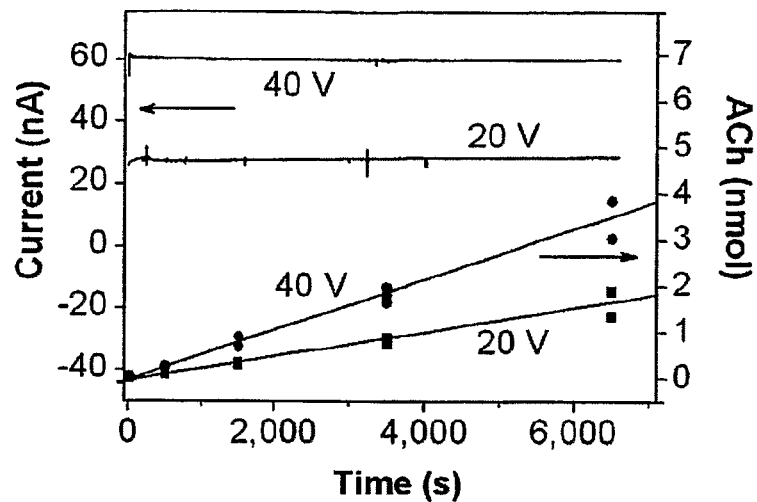
FIG. 11a is a diagram showing typical electric currents and acetylcholine concentration vs time in an ion transport device with an ion transport interface 106 of dimension 10 μm.
Figure 11B:
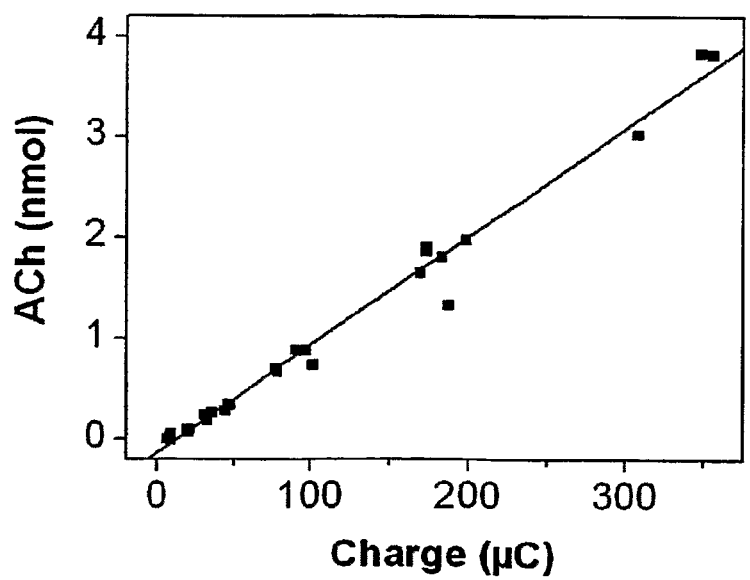
FIG. 11b is a diagram showing the correlation between the transported amount of acetylcholine and total electric charge in an ion transport device with an ion transport interface 106 of dimension 10 μm.
Figure 11C:
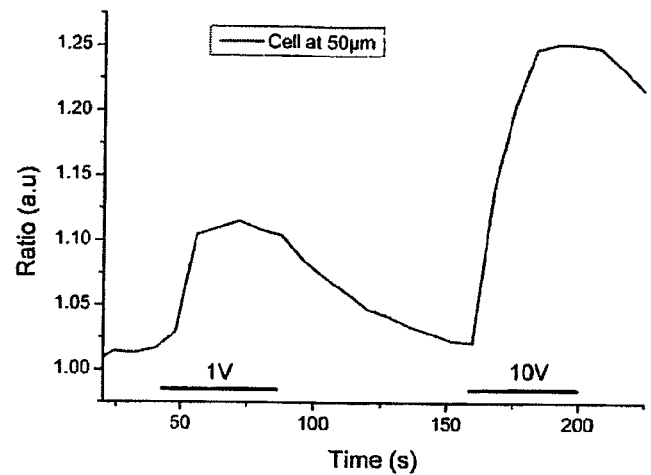

FIG. 11c is a diagram showing intracellular calcium response from SH-SY5Y cells cultured within 200 μm from the ion transport interface 106 (dimension 10 μm) when stimulated with acetylcholine delivered by the ion transport device.

Figure 11D:
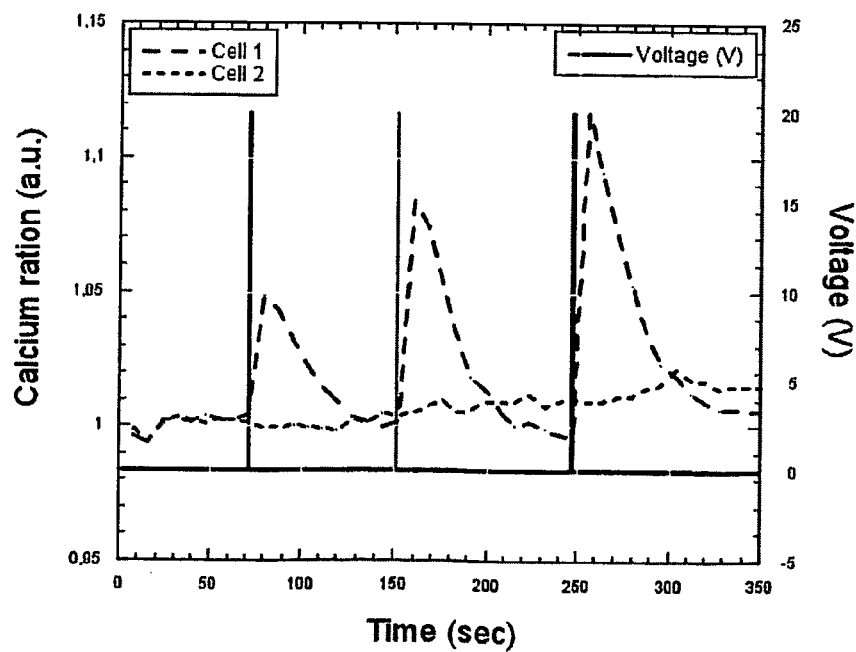

FIG. 11d is a diagram showing intracellular calcium response from SH-SY5Y cells cultured within 200 μm from the ion transport interface 106 (dimension 10 μm) when stimulated with acetylcholine delivered in short pulses by the ion transport device.

DETAILED DESCRIPTION OF PREFERRED EMBODIMENTS

The embodiments described below are merely examples of possible device architectures and the present invention should not be limited thereto. The scope of the invention is as defined by the appended claims.

Embodiment 1

Figure 1A:
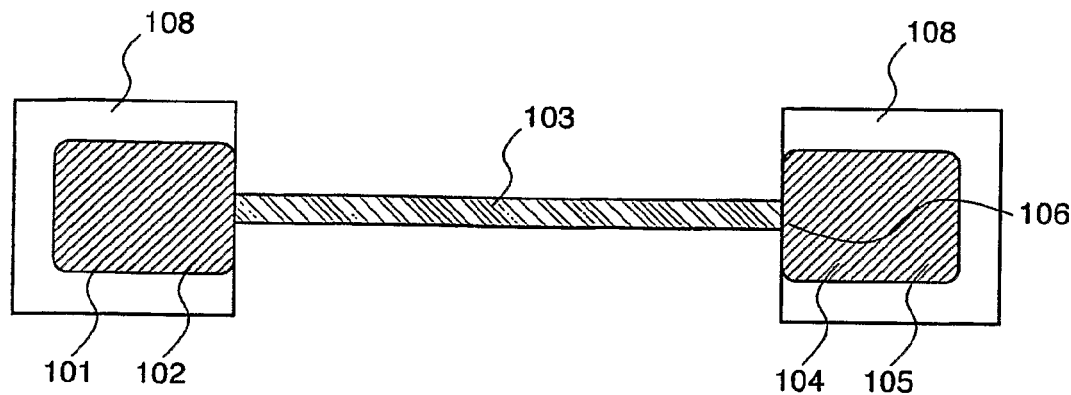
FIGS. 1a to 1k are schematic top and side views illustrating different embodiments of the device for ion transport.
Figure 1B:
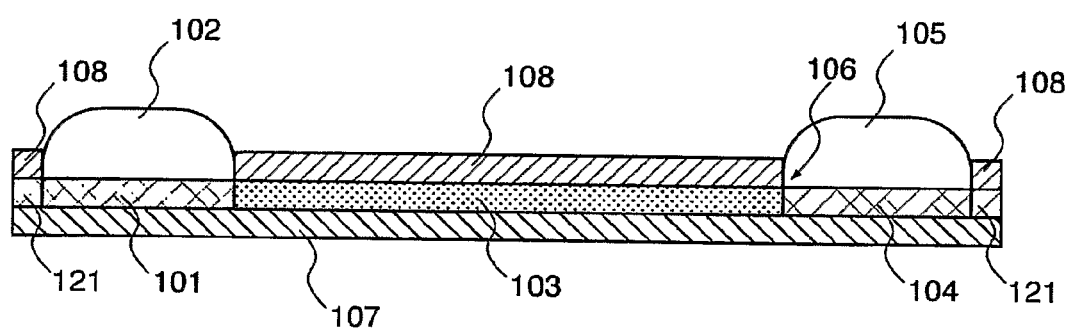
Figure 1C:
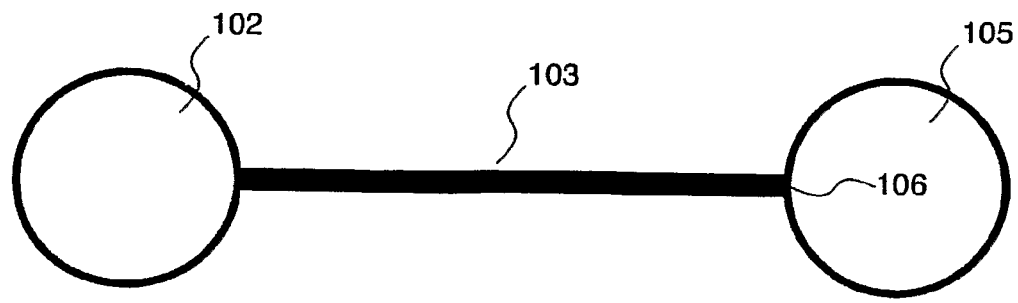

The inventors have found that it is not always advantageous with a device in which release of ions transported through the ion channel occurs along the entire edge of the target electrode in contact with the ion channel. The terms ion channel and ion-conductive channel are used interchangably in the present disclosure. As mentioned previously, it is of importance to be able to stimulate a single cell, a portion of a single cell, or a small cluster of cells instead of stimulating the whole side, or face, of a target electrolyte or cell culture area. According to a first embodiment, this problem may be solved by tailoring the dimensions of the ion channel or a portion of said ion channel so as to fit the size of a single cell, a portion of a single cell, multiple cells, or a cluster of cells. The interface between said ion channel and target electrode tailored to fit the size of a single cell, a portion of a single cell, multiple cells, or a cluster of cells is referred to herein as the ion transport interface. Such tailoring may for example be achieved by means of an ion channel cross section which is smaller than a surface portion or face of a target electrode. For example, an ion pump may have an ion channel cross section area which is smaller than the area of the target electrode facing the ion channel (FIGS. 1a and 1b). The ion pump comprises a source electrode 101, source electrolyte 102, an ion channel 103, a target electrode 104, a target electrolyte 105, an electrolyte containment insulation 108, an electrical contact portion 121 and a substrate 107. The cross section of the ion channel 103, or at least the cross section of the ion channel at the ion transport interface 106, has dimensions that are tailored to release ions on the scale of a single cell, a portion of a single cell, or a cell cluster. FIG. 1c is a simplified schematic version of the device illustrated in FIG. 1a. This kind of simplified drawing will be used to describe more complex structures below. The terms ion channel and ion-conductive channel are used interchangably in the present disclosure. The source electrolyte 102 and the target electrolyte 105 are labelled, but to each electrolyte is an associated electrode not shown in the simplified drawing.

Figure 1D:
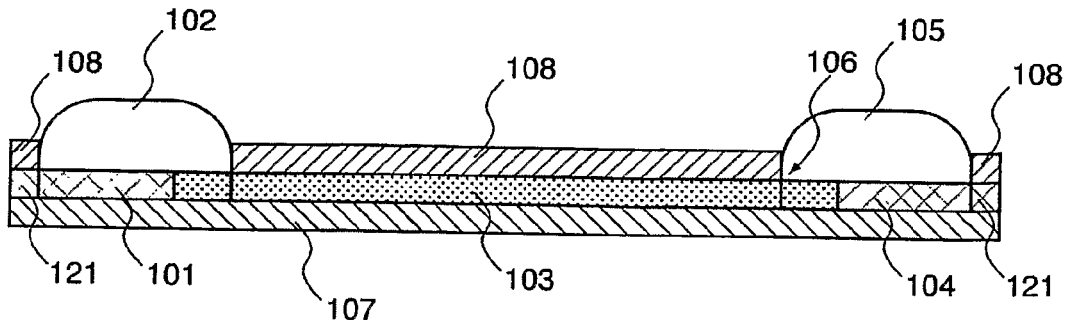
Figure 1E:
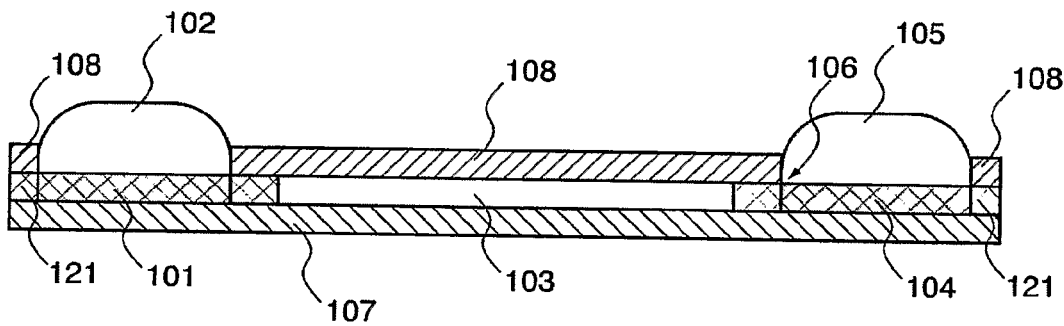
Figure 1F:
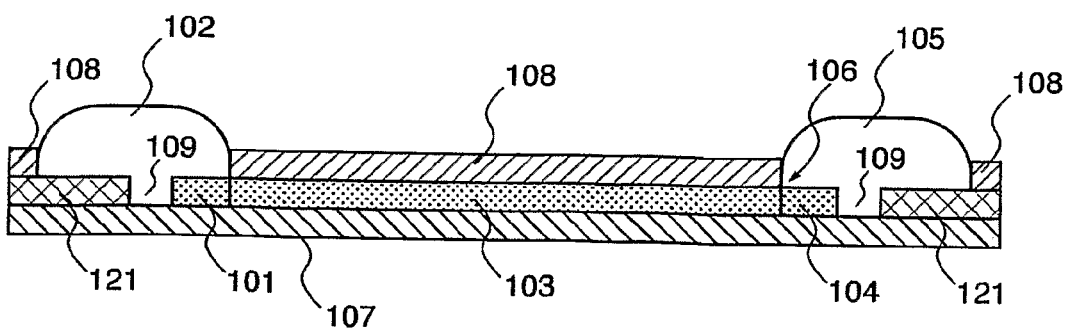
Figure 1G:
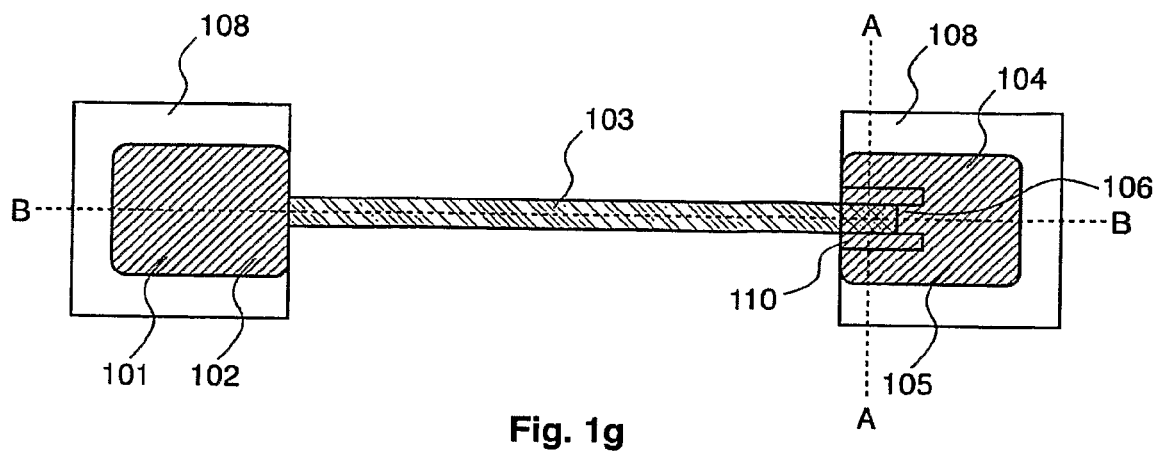

The electrodes 101 and 104 comprise an electrochemically active material, for example PEDOT:PSS or any other electrochemically active material mentioned herein, an ion transport portion, which is arranged of ionically conductive material and an ion passage surface—the surface of said ion transport portion through which ions may pass to or from the electrolyte. The total amount of ions that can be transported from the source electrolyte to the target electrolyte (the transport "capacity") depends partly on the type of material and partly on the amount of material in the electrodes 101, 104. The volume of the electrodes may be tailored to achieve the desired capacity. Typically the surface area of the electrodes is in the range of 1 cm$^2$ to 25 cm$^2$, with a thickness in the range 10 nm to 1 mm, preferably 100 nm to 100 μm). However, the surface area of the electrode may be reduced down to 100 μm$^2$ or increased to 1 dm$^2$. The ion channel 103 comprises an ionically conducting and electrically insulating material, e.g. over oxidized PEDOT:PSS. The ion pump may be at least partially covered by an electrolyte containment insulation 108, for example SU-8, polyimide, PDMS, or any other material which will provide physical, ionic and/or electric insulation of the device or parts thereof, with openings for the electrolytes 102, 105 and for electrical contacts to the electrical contact portion 121 (not shown in the figures). The electrical contact portion 121 may comprises an electrically conducting material, for example conducting polymers or metals. The openings in the electrolyte containment insulation 108 may serve to contain the electrolytes 102, 105. Additional structures may be added on top of the electrolyte containment insulation 108 to increase the space for such containment of the electrolytes. The source electrode 101 is in contact with the source electrolyte 102 and the target electrode 104 is in contact with the target electrolyte 105. The ion channel 103 is in contact with both the source and target electrodes 101, 104 (FIGS. 1d-f). In the embodiments presented in FIGS. 1b and 1d-f, the ion transport interface 106 is the interface between the target electrode 104 and the ion channel 103. In the figures, the ion transport interface is located at the bottom-left-most edge of the target electrode 104 in the direction of the source electrode 102.

The parts of the electrodes in contact with the ion channel need not be the same on both sides of the ion channel. The ion channel which is in between the electrodes 101, 104 may be covered by an electrolyte containment insulation 108, which may be composed of several different materials and parts. The insulation of the ion channel is not shown in the figures seen from above. The electrodes and ion channels may be directly or indirectly attached to a solid insulating support 107, such as a glass support or a flexible insulating support, such as a support comprising, or being made of, a plastic film or paper.

The ion pump is operated by applying a voltage between the source electrode 101 and the target electrode 104. The applied voltage drives redox reactions at the electrodes 101, 104. In the case of a positive voltage between the source electrode 101 and target electrode 104, i.e. using the source electrode 101 as the anode and target electrode 104 as the cathode, the source electrode 101 may be oxidized and the target electrode 104 may be reduced. In the case of a negative voltage between the source electrode 101 and target electrode 104, i.e. using the source electrode 101 as the cathode and target electrode 104 as the anode, the source electrode 101 may be reduced and the target electrode 104 may be oxidized. As a non-limiting example, utilizing a positive voltage (source electrode as anode) and PEDOT:PSS as electrode material, the chemical reaction may be represented as (M$^+$ is a mobile cation):

Source electrode: PEDOT$^0$+M$^+$PSS$^-$→PEDOT$^+$PSS$^-$+M$^+$+e$^-$

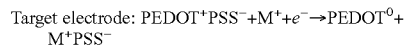
Target electrode: PEDOT$^+$PSS$^-$+M$^+$+e$^-$→PEDOT$^0$+M$^+$PSS$^-$ As can be seen from the reaction scheme, the reactions require that an electron is transferred from the source electrode 101 to the target electrode 104 at the same time as a cation is transferred through the ion channel from the source electrode 101 to the target electrode 104. Once the ions reach the target electrode 104 they are released into the target electrolyte 105 by diffusion or other means. This is the mechanism behind the ion transport in the device which also explains why it is possible to determine the amount of transported ions from the electrical current: each electron corresponds to one ionic charge. If anions are pumped through the ion channel instead of cations, the reaction scheme is similar and the relationship between electrical current and transported ions holds. The rate limiting process is ion transport since electrons are more easily transported. The rate at which ions are transported through the ion channel may be approximately proportional to the voltage applied between the source and target electrodes in the range of typical voltages 0-20 V. An inherent advantage of a device according to the invention which utilizes conducting polymers is the low voltage required to effect ion transport from a source to a target electrolyte.

The magnitude and polarity of the voltages to be applied in the inventive device and method may vary depending on a number of factors, such as choice of electrode material(s), the ions to be transported, the distance over which the ions are transported, etc. The polarity of the applied voltages will easily be selected by a person skilled in the art, taking into account the type of charge (positive or negative) of the ion to be transported. The magnitude of the voltage to be applied may in the light of the present invention easily be determined in order to transport a desired amount of ions.

The voltage applied across the ion channel may for example be within the range of from about 0.01 V to about 100 V. The optimal voltage to be applied between electrodes will depend on the characteristics of the electrode material used, the electrolyte used, the ion(s) to be transported and the manner in which the voltage is applied. However, the voltage is preferably in the range of from 0.01 V to 100 V, more preferably in the range of from 0.01 V to 20 V.

Figure 1H:
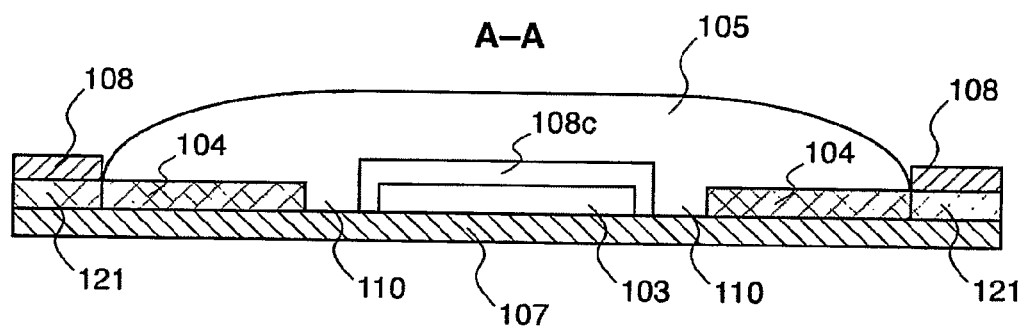
Figure 1I:
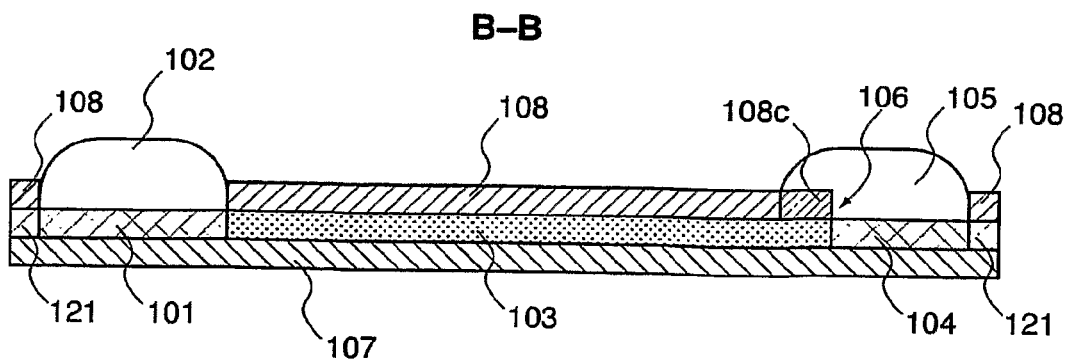
Figure 1J:
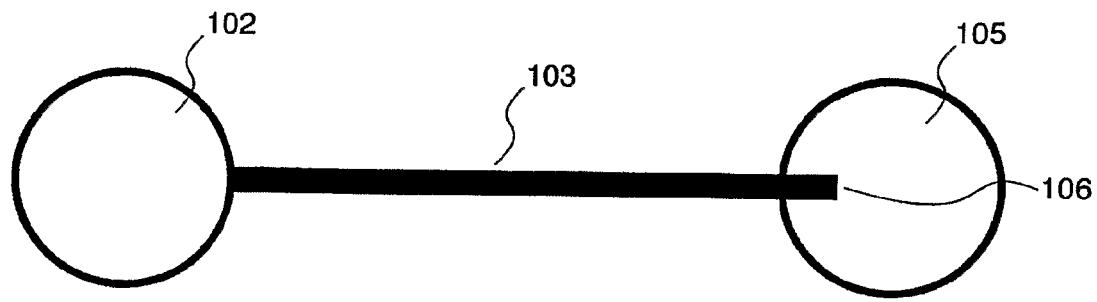

In FIGS. 1a-c the ion transport interface 106 of the ion channel is positioned at a side face of the target electrode 104 and target electrolyte 105. In some cases one would prefer to position this ion transport interface at a position at the electrolyte bottom surface, i.e. the interface between the electrolyte and its underlying electrode. In FIGS. 1g-j, another embodiment of the invention is shown, wherein the ion transport interface 106 of the ion channel is positioned near the centre of the target electrolyte's 105 bottom surface. It may of course be positioned at any position at the electrolyte bottom surface or electrode area 104. It may be necessary to insulate the ion channel from the electrolyte 105 and electrode 104 to prevent leakage of ions and achieve an ion transport interface inside the electrolyte. FIG. 1h shows a cross section of the embodiment shown in FIG. 1g and illustrates an example of how an insulation of the ion channel may be achieved. The ion channel 103 may be physically separated from the target electrode 104 along the sides 110 of the ion channel to prevent leakage of ions to the target electrode 104 and target electrolyte 105 (FIG. 1h). Furthermore, the ion channel may be insulated from the electrolyte by an insulating layer 108c which may be of the same material as the electrolyte containment insulation 108. The ion transport interface 106 of the ion channel is positioned where this insulating layer 108c ends. FIG. 1i shows the cross section B-B from FIG. 1g, in which the channel insulation 108c extends into the electrolyte to position the ion transport interface inside the target electrolyte 105. FIG. 1j is a simplified way of drawing 1g.

In some embodiments, the ion transport interface may for example have a cross sectional area in the range of 10 nm$^2$-10 mm$^2$, such as 10 nm$^2$-10000 μm$^2$, such as 10 nm$^2$-100 μm$^2$, such as 10 nm$^2$-1 μm$^2$, such as 10 nm$^2$-10000 nm$^2$, or such as 10 nm$^2$-100 nm$^2$. In other embodiments the ion transport interface may have a cross sectional area which is smaller than 10 nm$^2$.

Figure 1K:
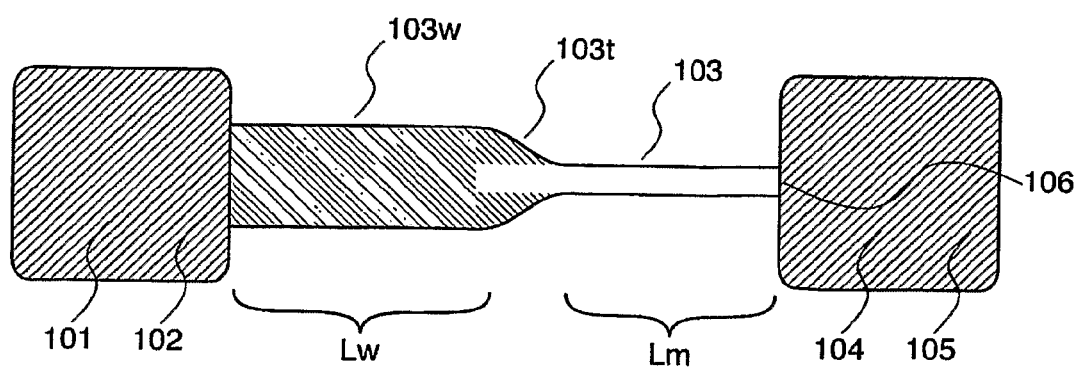

Two embodiments of the invention may have the same cross section area of the ion transport interface of the ion channel, but very different requirements for the pumping rate of ions. The pumping rate may be controlled by the voltage applied between the source and target electrodes, as described above. However, the required voltage may be impractically low or impractically high in some applications. To address this problem, the cross section area of the ion channel may be varied along the extension in the longitudinal direction of the ion channel or the ion channel impedance (resistance to the flow of ions) of the material of the ion channel may be tailored. As a non-limiting example, the width of the ion channel may vary between its different parts or longitudinal sections (FIG. 1k), The ion channel impedance may be tailored to fit the requirement of the application while maintaining the size of the ion transport interface of the ion channel. For instance, if an application requires a high pumping rate, only the "target" end of the ion channel may be scaled down to the desired size for the ion transport interface of the ion channel. This will result in an overall reduced ion channel impedance. The same effect may be achieved by using a material with lower impedance or by increasing the width of the ion channel, thus increasing the cross section and thereby lowering the impedance. This would enable high pumping rates with moderately low voltages combined with a small ion transport interface area. As an example, the ion channel may have two sections, 103w and 103, having different widths, wherein the length of the first section 103w is Lw and the length of the second section 103 is Lm. The lengths and widths of the sections 103w, 103 may be tailored to achieve a desired ion channel impedance. If the material properties are known, the skilled person may easily predict the ion channel impedance. The transition region between the two different ion channel widths 103t may be gradual (FIG. 1k) or just a step in ion channel width. As a non-limiting example, the ion channel widths may be tailored using a tapering geometry for the transition region of the ion channel 103t. The skilled person realizes that further geometries and materials for tailoring the ion channel are within the scope of this invention. The technique described in this embodiment is applicable to all architectures with ion channels described in the present disclosure.

Embodiment 2

Figure 2A:
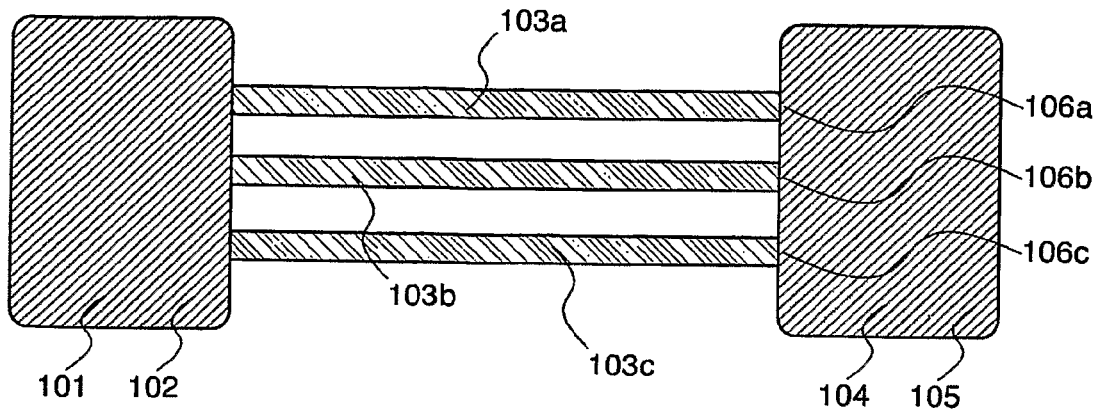
FIGS. 2a to 2d are schematic top views of an ion transport device having three separate ion-conductive channels.
Figure 2B:
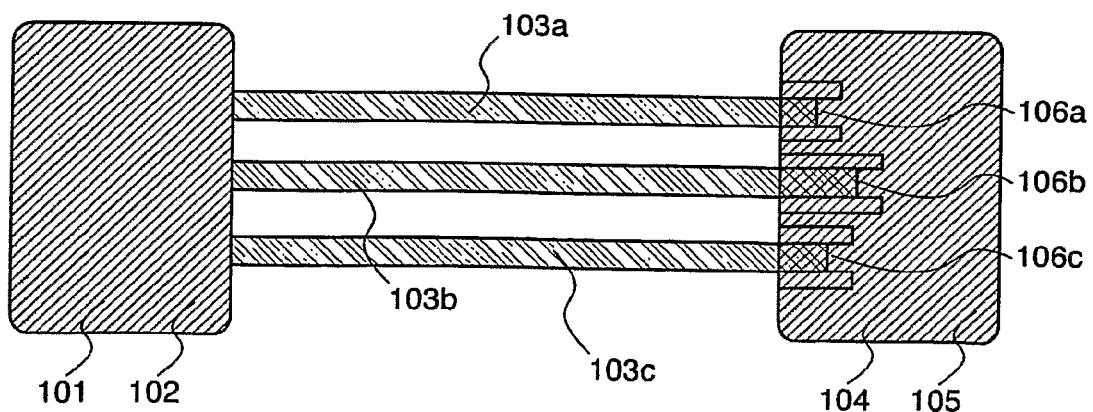
Figure 2C:
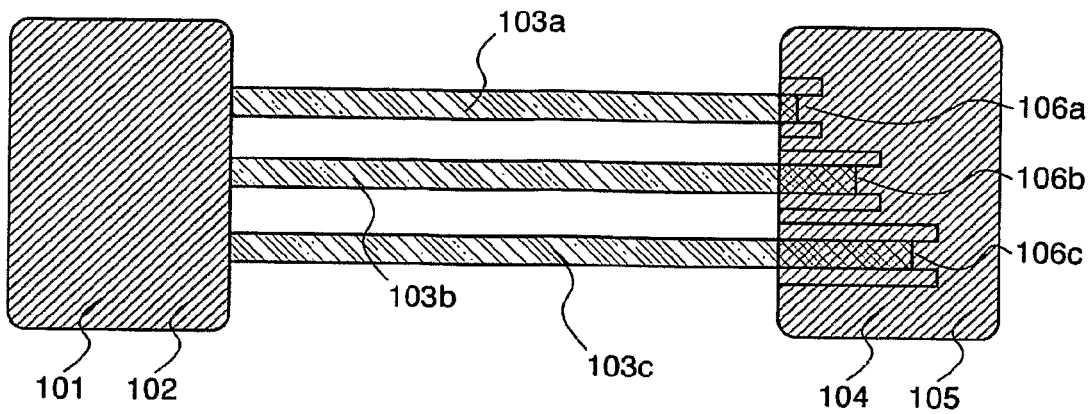
Figure 2D:
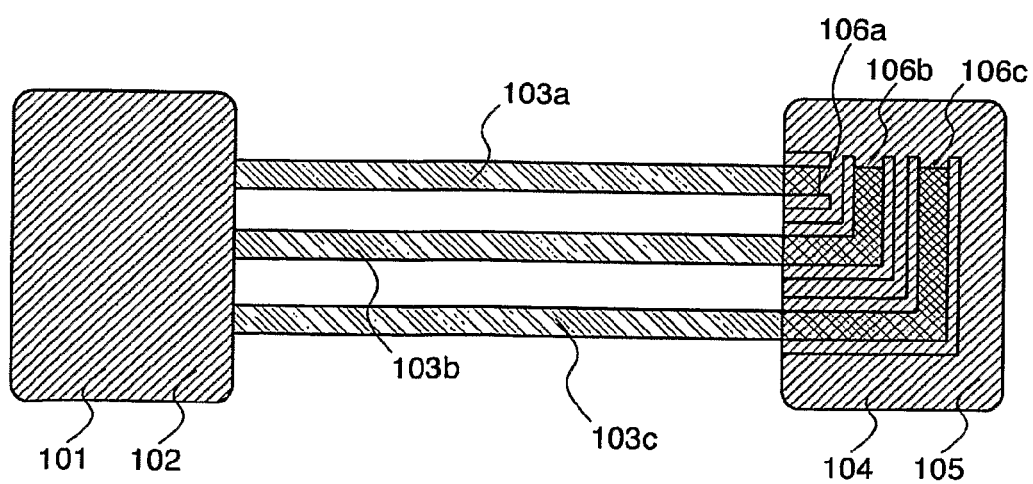

In the above embodiments, only one cell or cell cluster at the target electrode 104 could be stimulated. In this embodiment of the invention, multiple ion channels may be positioned between a single source electrode 101 and a single target electrode 104. FIG. 2a illustrates an embodiment having three ion channels 103a-103c which may be positioned so as to form separated ion transport interfaces 106a-106c (similar to embodiments illustrated in FIGS. 1a-c). FIGS. 2b-d illustrate embodiments wherein the ion transport interfaces 106a-106c are positioned at different positions within the target electrolyte 105 (similar to embodiments in FIGS. 1g-j). The ion transport interfaces may form a pattern, for instance an array or line as illustrated in FIGS. 2b-d or be randomly positioned over the target electrode surface 104. Although the embodiments illustrated in FIGS. 2a-d only have three ion channels, the number of ion channels may be any number more than one and may be chosen with regard to the application or technical fabrication limitations. In the configuration according to the present embodiment, the on channels can not be addressed separately, as the driving voltage applied between the source electrode 101 and target electrode 104 cannot distinguish between the various ion channels 103a-c. When using embodiments such as those in FIGS. 2a-d, ions will be pumped through all ion channels simultaneously. In order to select which ion channel(s) 103a-c in devices such as those depicted in FIGS. 2a-d should transport ions and which should not, or which should transport ions more slowly, means to control the pumping rate through each ion channel is necessary.

When there are several ion channels in parallel 103a-c with different lengths, as illustrated in FIGS. 2b-d, the pumping rate of ions may vary between the ion channels because of the difference in ion channel impedance between them. In a preferred example, the ion channel impedance is the same for all the ion channels of different lengths. This may be achieved by using the technique described in embodiment 1 above. For example, by making part of the length of the longer ion channels wider than the shorter ones, it is possible to make the ion channel impedance the same for all the ion channels 103a-c. Alternatively, by choosing different impedances for different ion channels 103a-c, a time delay of delivery of different species at the different ion transport interfaces 106a-c may be generated and/or the delivery rate may be controlled.

Embodiment 3

Figure 3A:
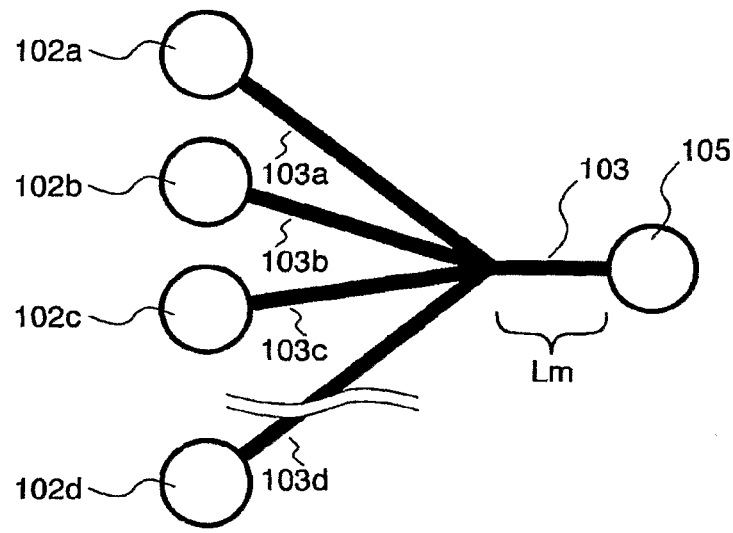
FIGS. 3a and 3b are schematic top views of an ion transport device having at least four ion channel portion, which merges into a common ion-conductive channel.
Figure 3B:
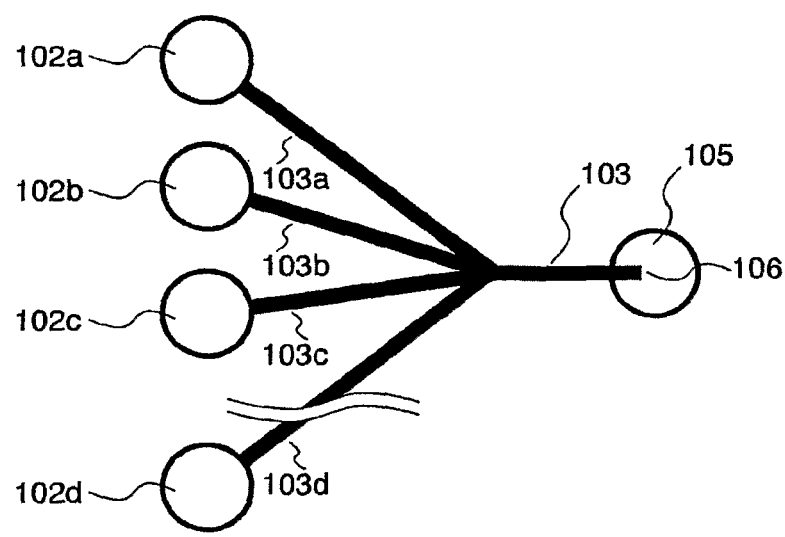

The inventors have found that the release of the transported ions may not be restricted to a single ion species at each ion transport interface. As mentioned above, cells may be stimulated by a large variety of biologically active molecules, or "biomolecules", and it is important to be able to stimulate cells with many different ion species either simultaneously or consecutively. To address this problem, it is provided a third embodiment, wherein several ion channels 103a-d from different source electrodes with corresponding source electrolytes 102a-102d may be merged to form one ion channel 103 before entering the target electrolyte 105 (a scheme of the third embodiment is shown schematically in FIG. 3a). Any number of ion channels with corresponding source electrodes and source electrolytes may be merged together as shown in FIG. 3a. The ion channels 103a-103d merge together a distance Lm from the target electrode 104. The distance Lm may be varied, even down to zero length, and in one preferable configuration Lm may be between 10 μm and 500 μm. Merging several ion channels together in one point is a non-limiting example of the invention. The skilled person realizes that further ways of merging ion channels together in different steps or other geometries to achieve one or several ion channels that connect to the target electrode 104 are within the scope of the present invention. When different ion species are placed in the different source electrolytes 102a-d, this architecture enables simultaneous or sequential pumping of different ion species from the source electrolytes 102a-102d into one ion transport interface in the target electrolyte 105. The pumping rate of the different ion species may be controlled individually by the addressing voltage applied between each source electrode and the target electrode. Temporal resolution of the ion flows may also be achieved by varying the addressing voltages over time.

In another variation of the third embodiment of the invention, the ion channels 103a-d are merged into one ion channel 103 which has an ion transport interface 106 at a position inside the target electrolyte. The placement of the release point is achieved in the same way as in the variants of Embodiment 1 presented in FIGS. 1g-j.

Embodiment 4

Figure 4A:
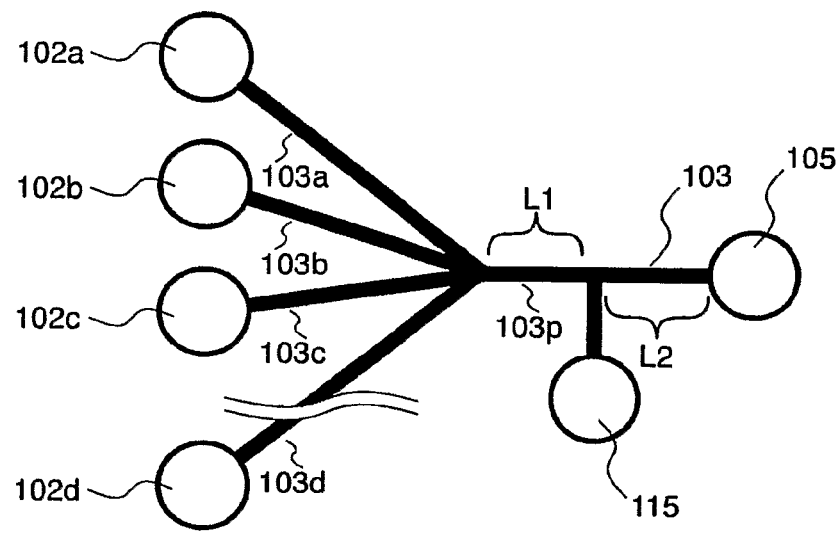
FIGS. 4a and 4b are schematic top views of an ion transport device provided with a waste channel.

It has been a problem as discovered by the inventors that release of relevant source ions has been delayed because of the time needed for the ions to migrate from the source electrolyte 102 to the source electrode 101 through the ion channel 103 to the target electrode 104 and into the target electrolyte 105. It is important to have a fast release of the source ions after turning on the device to achieve precise control of cell stimulation. Another problem may be that when turning on a device, other ion species than the intended source ions are initially released until the intended source ions have passed through the ion channel 103. These problems induce an uncertainty about the amount of intended source ions that are transported to the target electrolyte since some of the electric current used to determine the number of transported ions correspond to other ion species than the intended. To address this problem, it is provided a fourth embodiment, wherein a waste electrolyte 115 with corresponding waste electrode may be added to the device as illustrated in FIG. 4a. The waste electrolyte 115 with corresponding waste electrode is added a distance L1 from the merging point of the ion channels 103a-d and at a distance L2 from the target electrolyte 105 with corresponding electrode. The distances L1 and L2 may be varied, even down to zero length, to achieve a desired functionality. As an example, by initially pumping from the source electrolytes 102a-d to the waste electrolyte 115, the ion channels 103a-d may be filled with the intended source ions. Subsequently, when switching to pumping from the source electrolytes 102a-d to the target electrolyte 105, the intended source ions are already in the ion channels 103a-d, 103p and their release into the target electrolyte 105 will be faster than if not using this configuration. Since very few unwanted ions are pumped with this configuration, the amount of intended source ions which have been released may accurately be determined from the integrated electrical current through the device. As an example, both L1 and L2 may be between 0 μm and 5000 μm, and in a preferable configuration, L1 is 0 μm and L2 is between 10 μm and 500 μm. In this preferable configuration, all ion channels may be loaded without getting a mixture of ions since L1 is 0 μm. The release of ions into the target electrolyte 105 will also be fast because L2 is short (between 10 μm and 500 μm). If the configuration comprises several ion channels which have separate ion transport interfaces 106 in the target electrolyte 105 (FIGS. 2a-d, 5, 6), one waste electrolyte 115 with corresponding waste electrode may for example be added to each ion channel.

Figure 4B:
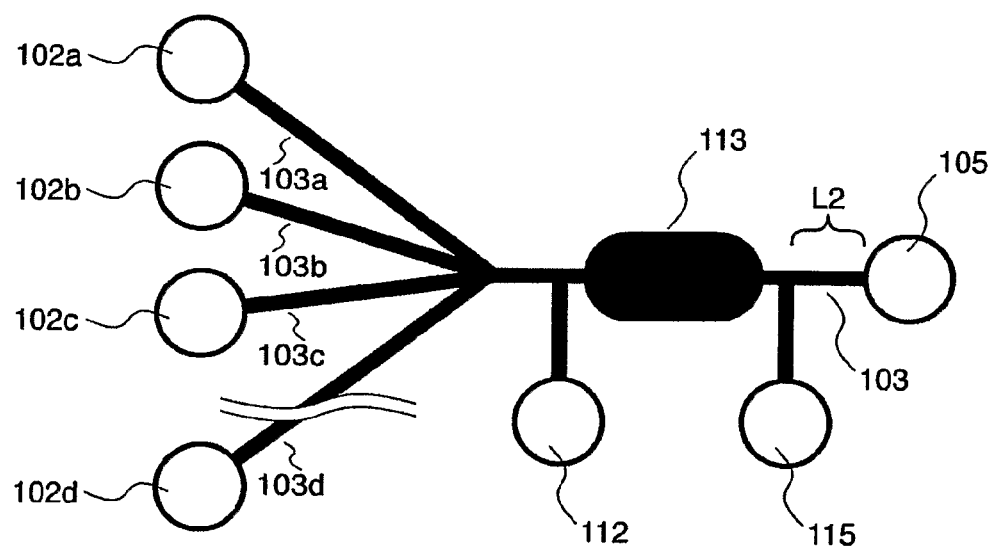

The amount of released ions may be determined through measurements of the electronically current(s) in the circuit(s) connecting the source and target electrodes. However, accurate measurements of small currents require expensive and calibrated equipment. To address this problem, it is provided a fourth embodiment, wherein pre-loading regions may be utilized to release specific amounts of ions without the need to monitor the electronic current through the external circuit during transport. A pre-loading region is a region of the ion channel comprising an amount of material which has a specific capacity for storing ions. The amount of material in the region and the properties of the material determine its capacity for storing ions. A pre-loading region 113 may be incorporated along the ion channel 103 between the source electrolytes 102a-d with corresponding electrodes and the target electrolyte 105 with corresponding electrodes (FIG. 4b). Any number of source electrolytes with corresponding electrodes may be connected through ion channels 103a-d to the entry point of the pre-loading region 113. Further, a waste electrolyte 115 with corresponding waste electrode may be connected on the target electrolyte side near the end of the pre-loading region 113, and a flush electrolyte with corresponding flush electrode 112 may be connected near the entry point of the pre-loading region 113. The pre-loading region 113 may be loaded with the intended source ion specie (s) by pumping from the source electrolyte(s) 102a-d to the waste electrolyte 115, i.e. by a driving voltage applied between the source electrodes and the waste electrode (not shown in FIG. 4b). Subsequently, when the pre-loading region 113 is filled, its content(s) may be released into the target electrolyte 105 by pumping from the flush electrolyte 112 to the target electrolyte 105, i.e. by a driving voltage applied between the flush electrode and the target electrode (not shown in FIG. 4b). As an example, the flush electrolyte 112 may preferably contain a biologically inert electrolyte since it is used for flushing the ion specie(s) from the pre-loading region 113. Non-limiting examples of such an electrolyte are NaCl solutions, either at physiological or other concentrations, cell culture media and Ringer's solution. An ion pump device according to the present disclosure may comprise several pre-loading regions 113. These regions may be arranged in series, i.e. multiple pre-loading regions 113 along the path from source electrolyte 102 to target electrolytes 105. An advantage with such architecture is the possibility of delivering mixtures of different ion species sequentially with only one applied voltage. The pre-loading regions 113 may also be arranged in parallel, i.e. multiple pre-loading regions 113 that may be individually addressed to independently deliver ions. In such architecture, each pre-loading region 113 may be controlled individually and released through one or several ion transport interfaces 106 in the target electrolyte with temporal resolution. Multiple pre-loading regions 113 may also be arranged in a combination of the serial and parallel architectures described in this embodiment. As described previously in embodiment 1 the ion transport interface(s) may be located at arbitrary positions within the target electrode.

Embodiment 5

Figure 5:
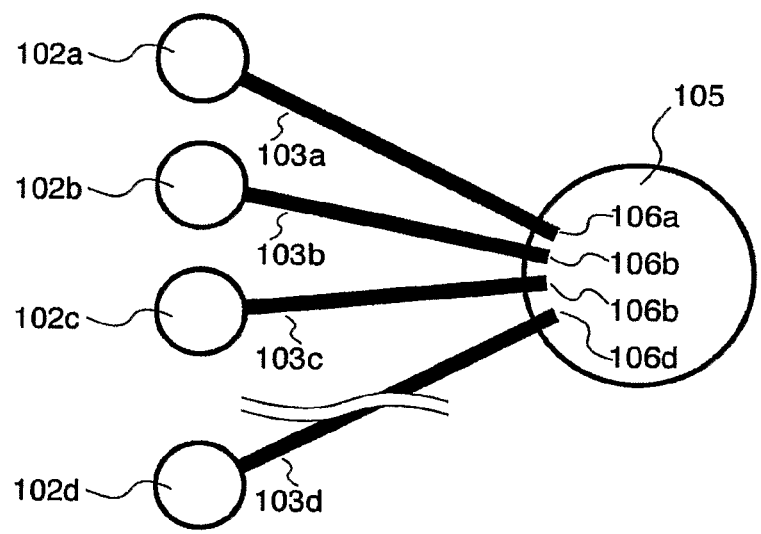
FIG. 5 illustrate four source electrodes and four separate ion-conductive channels which are connected to a common target electrode.

In a fifth embodiment, the ion pump device comprises multiple source electrolytes 102 with corresponding electrodes that each may have an individual ion channel 103 that enters into the target electrolyte 105 at individual and separated ion transport interfaces 106. As in the embodiments illustrated in FIGS. 2a-d, these ion transport interfaces may be located at any position in the target electrolyte 105 bottom surface. They may be ordered in a line, matrix, in any other pattern, or randomly. An example of such an ion pump device is illustrated in FIG. 5. In this example, the device comprises four source electrolytes 102a-d with corresponding electrodes and one target electrolyte 105 with corresponding electrode. Each source has a single ion channel 103a-d, and each of said ion channels have ion transport interfaces at different positions 106a-d in the target electrolyte 105. This configuration allows for the stimulation of four individual cells or cell clusters with up to four different ion species A, B, C, and D and at four different locations in the cell culture. Therefore, this embodiment may result in both temporal and spatial control of the stimulation by means of activation of the appropriate ion channel by applying a potential to the corresponding electrode at the intended time.

Embodiment 6

Figure 6A:
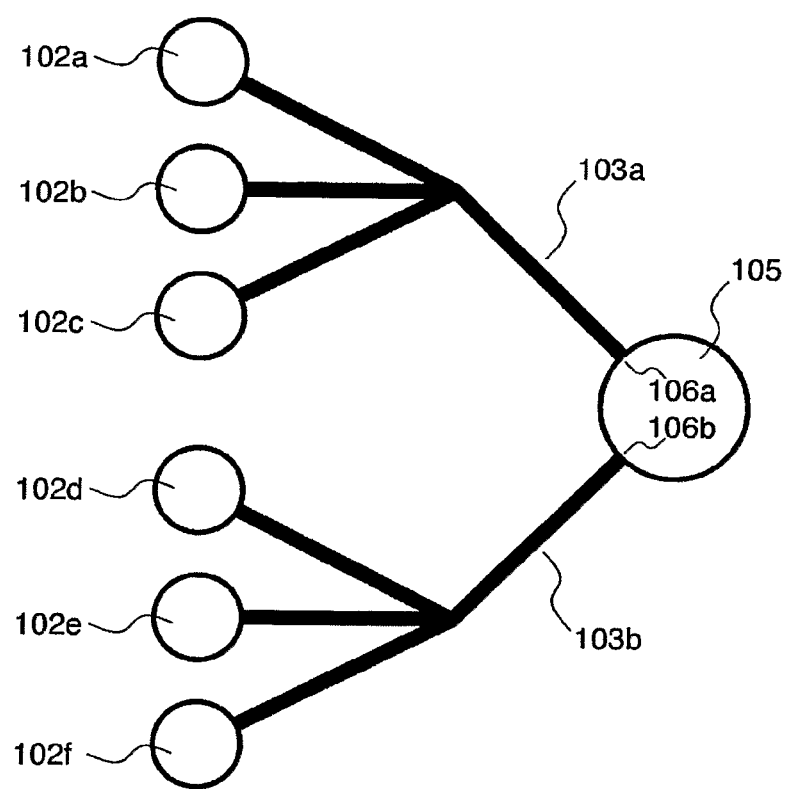
FIGS. 6a and 6b are schematic top views of further embodiments of the ion transport device.

The concepts of the previous embodiments may be combined into what may be called multiplexing or matrix devices, i.e. combinations of one or more of any of the embodiments illustrated in FIGS. 1a-k, 2a-d, 3a-b, 4a-b and/or 5. An example of one such combination is illustrated in FIG. 6a, but any other possible combination apparent to those of ordinary skill in the art is also covered by the present invention. In the example, the ion pump device comprises six source electrolytes 102a-f with corresponding electrodes, that converge into two ion channels 103a and 103b, which in turn have ion transport interfaces at two separate positions 106a and 106b in the target electrolyte 105. The source electrolytes 102a-f may comprise electrolytes A, B, C, D, E and F, respectively, and thus ion species from electrolytes A, B, and/or C may be delivered at an ion transport interface 106a, and ions from electrolytes D, E, and/or F may be delivered at an ion transport interface 106b. As another example, the source electrolytes 102a-f may contain electrolytes A, B, C, A, B and C, respectively, and thus ions from electrolytes A, B, and/or C may be delivered at both an ion transport interfaces 106a and 106b.

Figure 6B:
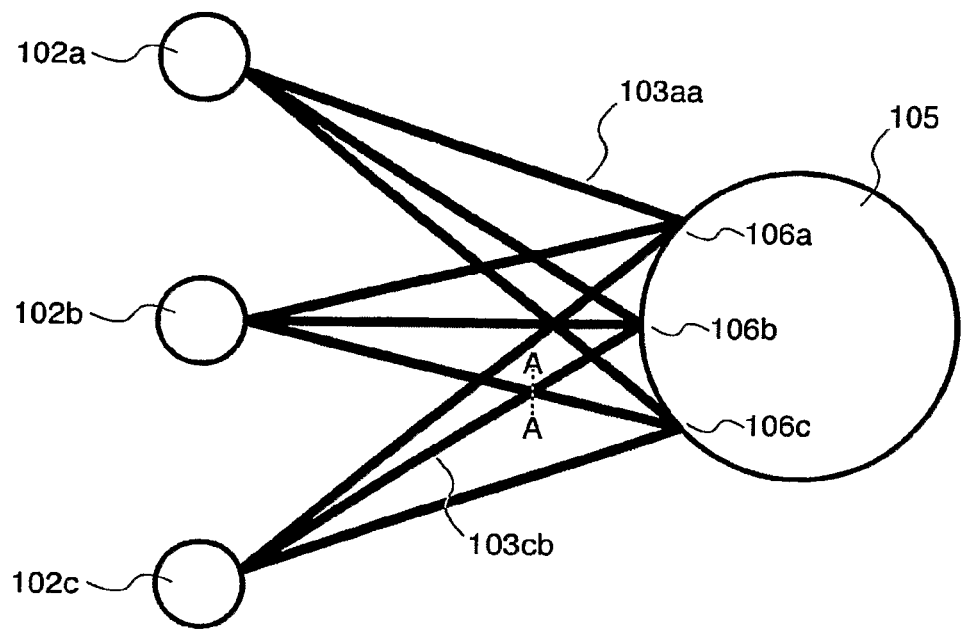

Yet another example of the multiplexing or matrix device is illustrated in FIG. 6b. In this example, the ion pump device comprises three source electrolytes 102a-c with corresponding electrodes, each being connected to the target electrolyte 105 with corresponding electrode at three separate positions 106a-c. The ion channels in this example may converge before or at the ion transport interfaces 106a-c, wherein each source electrolyte with corresponding electrode has a single ion channel to each of the three separate positions 106a-c at the target electrolyte with corresponding electrode. As an example, one ion channel 103aa may connect source electrolyte 102a with an ion transport interface 106a and another ion channel 103cb may connect source electrolyte 102c with an ion transport interface 106b.

The source electrolytes 102a-c may contain electrolytes A, B and C, respectively, and thus ion species from electrolytes A, B, and/or C may be delivered at the an ion transport interfaces 106a-c. Likewise as for the devices illustrated in FIGS. 2a-d, ions may be pumped simultaneously through all ion channels emanating from a given source electrolyte with corresponding electrode. For this reason, means for controlling the pumping rate through each ion channel would be necessary to select which ion channels emanating from a given source electrolyte with corresponding electrode that should transport ions and which that should not, or which that should transport ions more slowly.

Figure 6C:
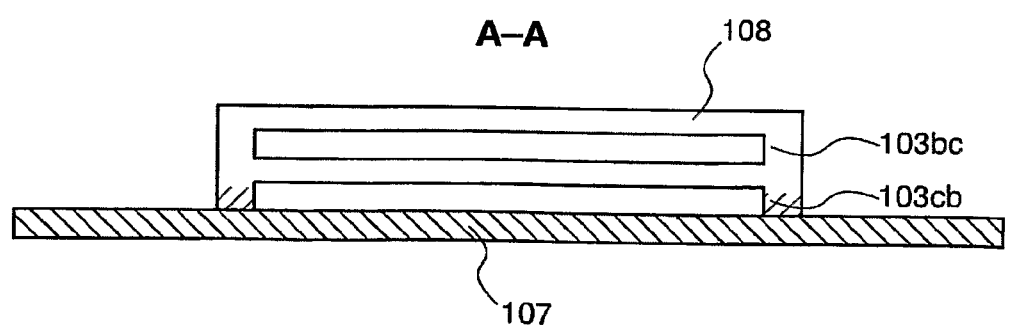
FIG. 6c is a cross sectional view taken along the line A-A in FIG. 6b.

In the embodiment of the ion pump device described above, the ion channels may have to cross each other. To address this problem, it is provided an example of the device, wherein a first ion channel 103cb may be arranged on a substrate 107 and covered by an insulating layer 108 and a second ion channel 103bc is arranged on top of the insulating layer so as to avoid contact between the first and second ion channels 103cb, 103bc. Further, the second ion channel 103bc may also be covered by the same or another insulating layer 108 (FIG. 6c).

Figure 6D:
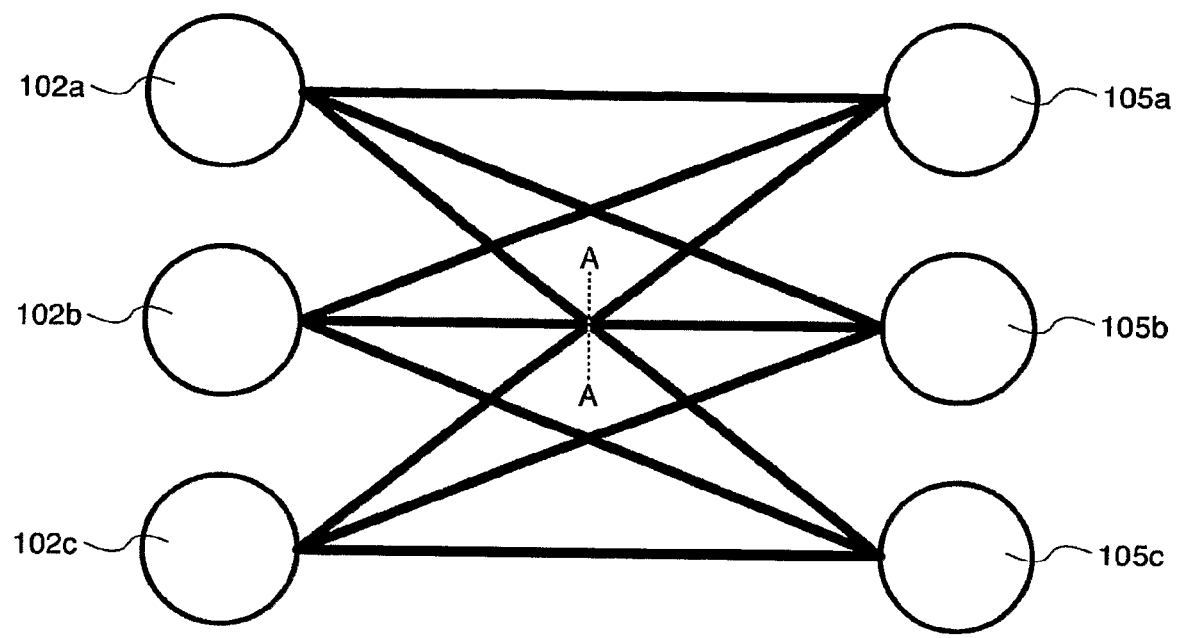
FIG. 6d is a schematic top view of an ion transport device having a matrix configuration.
Figure 6E:
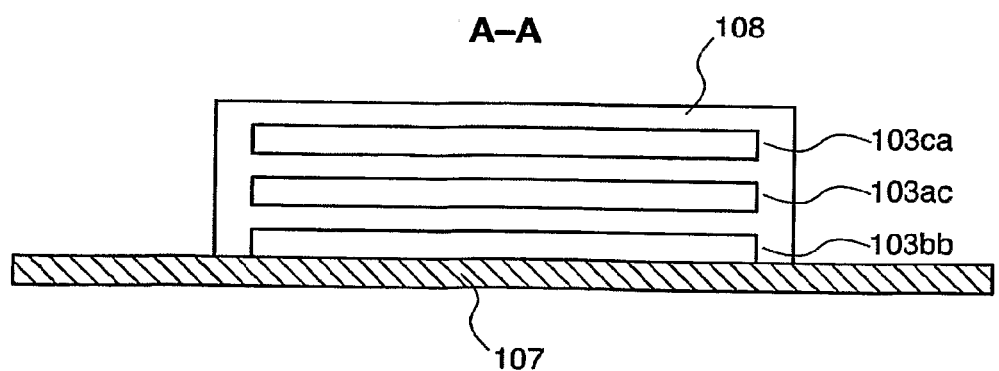
FIG. 6e is a cross sectional view taken along the line A-A in FIG. 6d.

In yet another example of the matrix or multiplexing ion pump device, similar to the device illustrated in FIG. 6d, the source electrolyte with corresponding electrode is divided into three separate source electrolytes 102a-c with corresponding electrodes and the target electrolyte 105 with corresponding electrode is divided into three separate target electrolytes 105a-c with corresponding electrodes. Each single source electrolyte 102a-c with corresponding electrode may be connected to all three target electrolytes 105a-c, each comprising its own target electrode system (not shown in the figure). An advantage of this arrangement is that different cell lines may be cultured in each target electrolyte or that each target electrolyte may comprise the same cell line but different cell culture media. As with the device illustrated in FIG. 6d, this device comprises several ion channel crossings. FIG. 6e illustrates a non-limiting example of how a three ion channel crossing may be fabricated, wherein three ion channels 103bb, 103ac, and 103ca are sandwiched between the substrate 107 and insulating layers 108, similar to the device illustrated in FIG. 6c.

In the devices described above, three source electrolytes with corresponding electrodes systems and/or three target electrolytes with corresponding electrodes systems are described. However, devices according to the invention may comprise any number of source and/or target systems. For example, the number of source and/or target systems may be chosen with regard to the desired application or technical fabrication limitations.

Figure 6F:
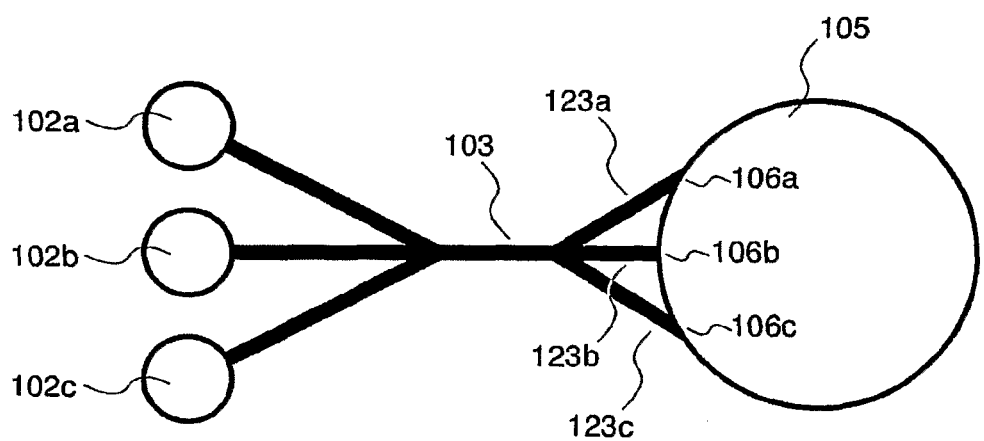
FIG. 6f and FIG. 7 are schematic top views of further embodiments of the ion transport device.

In FIG. 6f three different source electrolytes 102a-c with corresponding electrodes have their ion channels merged together to one channel 103, which is later split up into three different ion channels 123a-c with separated ion transport interfaces 106a-c in the target electrolyte 105 with corresponding electrode. The advantage with this structure is that a similar functionality as that of the device in FIG. 6b is achieved, but without crossing channels. By controlling the applied potential to the electrodes the mixture of ions in the channel 103 may be controlled. This mixture of ions may then be distributed to the separated ion transport interfaces 106a-c. The number of source electrolytes 102a-c with corresponding electrodes and the number of separated ion transport interfaces 106a-c may be chosen arbitrary.

Embodiment 7

Figure 7:
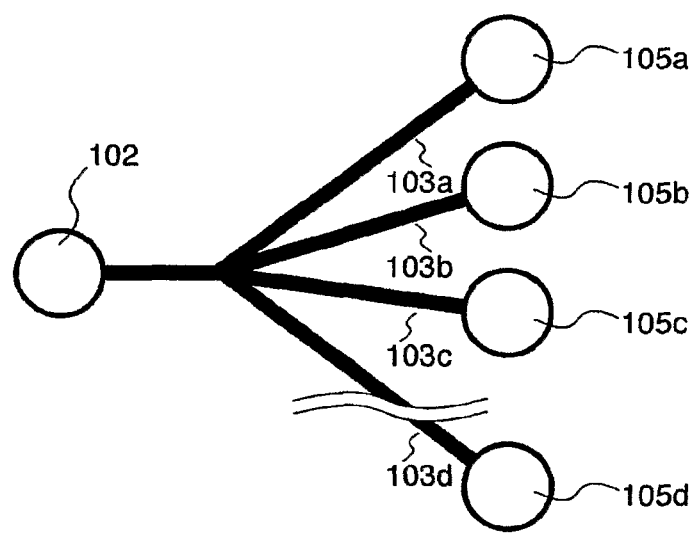

Most of the devices described in the above embodiments comprise a single target electrolyte with corresponding electrode and multiple source electrolytes with corresponding electrodes. However, it is also possible to have a single source electrolyte with corresponding electrode and multiple target electrolytes with corresponding electrodes. For example, most of the devices presented above could be arranged in reverse or be mirrored. For example, a single source 102 may individually provide ions to multiple target electrolytes 105a-c with corresponding electrodes through multiple ion channels 103a-c (FIG. 7). A non-limiting example of such an arrangement is a reversed/mirrored arrangement of that presented in FIG. 3a.

Embodiment 8

In the above embodiments, ions may be transported from a source electrolyte to a target electrolyte containing cells. In such embodiments, source ions may have been added to the source by external means, such as e.g. pipetting. In an eighth embodiment, the source electrolyte comprises cells that may produce and excrete biomolecules, such as ions, small molecules, nucleotides and proteins. These biomolecules that have been produced by the "source cells" may then be transported from the source electrolyte 102 through the ion channel 103 to the target electrolyte 105, e.g. in order to stimulate one or more cells or one or more cell clusters in the target electrolyte. The ion pump may have any of the above mentioned configurations, where any or all source electrolytes 102 (in the case of multiple sources) may comprise cells.

Figure 8A:
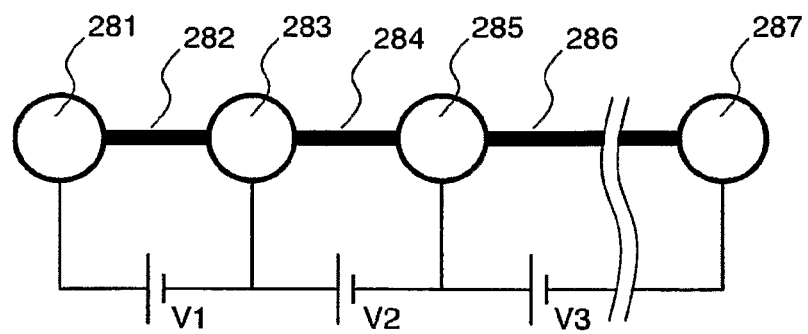
FIGS. 8a and 8b are schematic top views of an arrangement comprising at least three the ion transport devices arranged in series.

For example, an ion pump device may comprises at least three electrolytes with corresponding electrodes, such as four electrolytes with corresponding electrodes 281, 283, 285, 287 (FIG. 8a), but the device may also have fewer or more electrolytes with corresponding electrodes. The device may be interpreted as being three ion pumps in series, where the target electrolyte with corresponding electrode of the "first ion pump" functions as the source electrolyte with corresponding electrode of the "second ion pump", etc. For example, the device may comprise a first source electrolyte 281 with corresponding electrode connected to a second electrolyte 283 with corresponding electrode through a first ion channel 282, wherein the second electrolyte 283 with corresponding electrode in turn is connected to a third electrolyte 285 with corresponding electrode through a second ion channel 284 and the third electrolyte 285 with corresponding electrode is turn connected to a fourth, final electrolyte 287 with corresponding electrode through a third ion channel 286. In such device, biomolecules may be pumped from the first source electrolyte, which may or may not comprise cells, 281 through the first ion channel 282 to the second target electrolyte 283 that comprises cells by application of a voltage V1. The cells in the second electrolyte 283 may be stimulated by these pumped species and start to produce and secrete other biomolecules. These secreted biomolecules may then be transported from the second electrolyte 283 through the second ion channel 284 to the third electrolyte 285 by application of a voltage V2. The third electrolyte 285 may in turn comprise cells that may be stimulated by these biomolecules and also excrete biomolecules. These may then be pumped from the third electrolyte 285 through the third ion channel 286 into the fourth, final target electrolyte 287 by application of a voltage V3. The final target electrolyte 287 may then be used as a sensor in order to collect or analyze the finally transported biomolecules, or may also comprise cells. The potentials V1, V2, V3, may be applied simultaneously, sequentially, or in any other time pattern that may suit the cells/experiment.

Figure 8B:
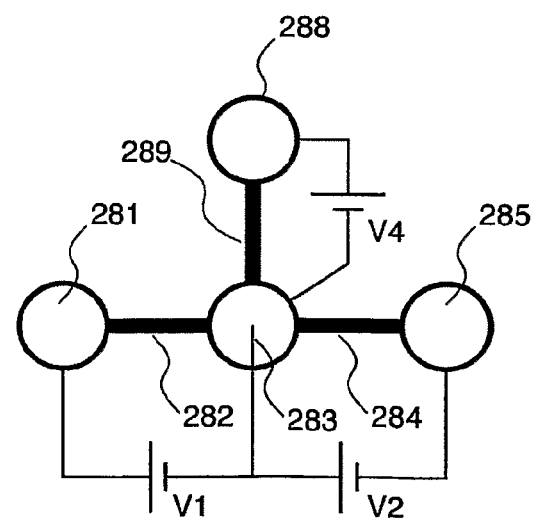

In another embodiment, several separate electrolytes with corresponding electrodes are all connected to a common target electrolyte with corresponding electrode. As an example, a first, second and third electrolyte 281, 288, 285 with corresponding electrodes are all connected to a fourth electrolyte 283 with corresponding electrode through a first, second and third ion channel 282, 289, 284, respectively (FIG. 8b). This geometry may be interpreted as two ion pumps in parallel that merge into a third. Biomolecules of species A may be pumped from the first source electrolyte 281 through the first ion channel 282 to the fourth electrolyte 283 by application of a potential V1. Biomolecules of species B may be pumped from the second source electrolyte 288 through the second ion channel 289 into the fourth electrolyte 283 by application of a potential V4. Further, the fourth electrolyte 283 may comprise cells that are stimulated by the species A and B. As a result of stimulation, the cells in the fourth electrolyte 283 may excrete other biomolecules that may be transported to the third (final target) electrolyte 285 through the third ion channel 284 by applying a potential V2. Similar to the device illustrated in FIG. 8a, the first and second electrolytes 281, 288 of may comprise cells that generate the biomolecules or the biomolecules may be added by external means, such as pipetting of a solution. The final target electrolyte 285 may be used as a sensor in order to collect or analyze the finally transported biomolecules, or may also comprise cells. The potentials V1, V2, V4, may be applied simultaneously, sequentially, or in any other time pattern that may suit the cells/experiment.

The number of ion channels, source and target electrolytes with corresponding electrodes in all the above mentioned examples are not in any way limiting to the scope of this invention. It is clear to the person skilled in the art from the present disclosure that many other variants are possible.

EXAMPLES

Preparatory Example 1

General Procedure for Fabrication of the Ion Transport Device

Devices were fabricated in a class 1000 cleanroom using photolithographic techniques and dry etching. Devices were conditioned in de-ionized water for 24 hours before use. A general procedure for fabrication of the ion transport devices is shown below.

As substrate, an Orgacon foil (AGFA) was used. Orgacon is a laminate consisting of a first layer of a polyester base and a second layer of PEDOT:PSS.

The Orgacon foil substrate was cleaned by washing in acetone followed by washing in water. The substrate was then baked at 110° C. for 5 min in order to dry the substrate before the etch process step below.

The photoresist (S1818 Microposit) was spin coated onto the Orgacon foil substrate. The photoresist was exposed using a mask-aligner (Suss Microtech MA 6/BA 6). Development was done with a Microposit MF319 developer. The non-covered areas of PEDOT:PSS were etched away using a reactive ion plasma consisting of $O_2$ and $CF_4$. The non-etched photoresist was removed using a Microposit remover 1112A. Another layer of photoresist was patterned in order to create opening where PEDOT:PSS was to be over-oxidized to create the ion channels. In the opening defined by the patterned photoresist, the PEDOT:PSS was exposed to 1% NaClO solution for 10 seconds. After rinsing in water the photoresist was removed using a Microposit remover 1112A. A layer of SU-8 (Microchem SU-8 2010) was spin-coated onto the patterned PEDOT:PSS. The SU-8 layer was baked by ramping the temperature from 50° C. to 110° C. during 16 minutes. The SU-8 layer was exposed using a mask-aligner (Suss Microtech MA 6/BA 6). A post-baking step was performed at 110° C. for 6 minutes. The SU-8 layer was developed using an XP SU-8 developer from Micro Resist Technology. The SU-8 layer was patterned in order to define areas for the electrolytes.

Preparatory Example 2

Fabrication of an Ion Transport Device with a Thicker Layer of PEDOT:PSS

The device in this example was fabricated as the device in Preparatory Example 1 except that a thicker layer of PEDOT:

PSS was obtained by spin-coating (at 1500 rpm) an additional layer of PEDOT:PSS prior to the masking and etching step. In this case a solution of Orgacon ICP 1010 mixed with 5% diethylene glycol and 0.1% zonyl was used. Spin-coating was followed by a baking step at 110° C. for 10 minutes.

Preparatory Example 3

A general procedure for fabrication of the ion transport devices using screen printing is shown below.

As substrate, a PET-foil (AS foil) from Heidelberg was used. Before printing, the substrate was heat treated in order to prevent shrinking of the substrate during curing of the inks.

The first printed layer was PEDOT:PSS (Clevios Sv 3: HC Starck) that was printed using a 77 web. Curing was made by baking at 145° C. for 2 min. The second printed layer was carbon (7102: DuPont) that was printed using a 77 web. Curing was made by baking at 145° C. for 2 min. The third printed layer was an UV-lacquer (UV 025 Täckvit: Sericol) that was printed using a 77 web. Curing was made by UV treatment.

In order to build chambers for the electrolyte, plastic rings with an outer diameter of 20 mm and an inner diameter of 18 mm with a height of 7 mm were glued to the substrate. Gluing was performed by applying the rings to the substrate before curing of the lacquer layer. By curing the lacquer layer after attaching the rings the lacquer will function as glue.

Example 1

Acetylcholine Transport Through a 100 μm Wide Ion Channel

The experiment was performed with a device fabricated as described in Preparatory Example 1 and as generally described in FIG. 3a, that is a ion pump device comprising two PEDOT:PSS source electrodes and one PEDOT:PSS target electrode. The ion-conductive channel in the form of 100 μm wide overoxidized lines of PEDOT:PSS, obtained as described in Preparatory Example 1, went from both source electrodes into a merging point forming a single ion channel which in its turn connected to the target electrode.

A solution of 40 μl of a source electrolyte consisting of 0.1 M acetylcholine cloride was deposited onto the device in such a way that it was brought into contact with one of the source electrodes. A solution of 50 μl of a target electrolyte consisting of 0.1 mM sodium cloride was deposited onto the device in such a way that it was brought into contact with the target electrode. The electrolytes were physically separated from each other as well as from the overoxidized line connecting the source and the target electrodes.

Figure 9:
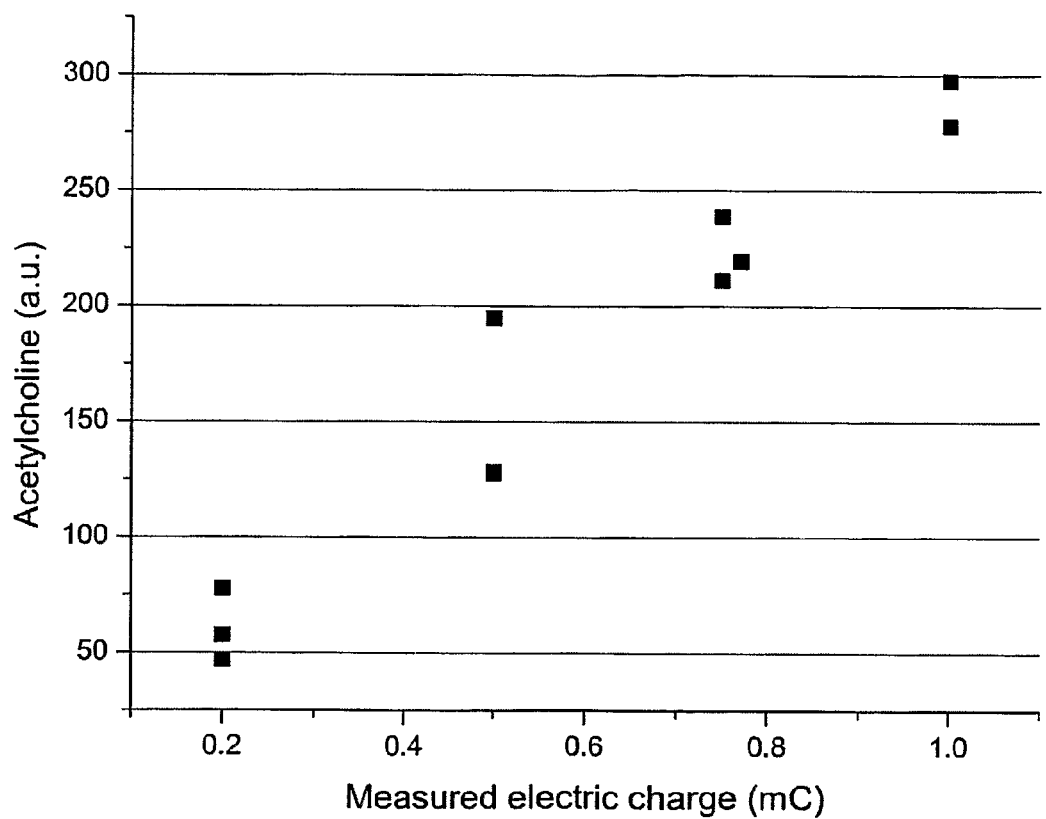
FIG. 9 is a diagram showing the correlation between the transported amount of acetylcholine and total charge.

Ion transport from the added source electrolyte to the target electrolyte was performed by applying a voltage between the source and the target electrodes, across the ion-conductive channel of the device. A voltage of 20 V was applied for different time periods and the electronic current between the source and target electrode was recorded. The resulting increase in acetylcholine ion concentration in the target electrolyte was measured and is presented in FIG. 9. It shows the correlation between the transported amount of acetylcholine and total charge (which is the measured electronic current multiplied by the applied time).

Example 2

$H^+$ Transport Through a 100 μm Wide Ion Conductive Channel with Ion Transport Interface at the Edge of the Target Electrode and Target Electrolyte The experiment was performed with devices fabricated as described in Preparatory Example 1 and as generally described in FIG. 5, that is an ion pump that comprises two PEDOT:PSS source electrodes and one PEDOT:PSS target electrode. The ion-conductive channels 103a, 103b in the form of 100 μm wide overoxidized lines of PEDOT:PSS, obtained as described in Preparatory Example 1, went from both source electrodes to the target electrode with seperated ion transport interfaces 106a and 106b at the edge of the target electrode and target electrolyte (see FIG. 10a and compare FIG. 5).

A source electrolytes 102a, 102b consisting of 40 μl 0.1 M HCl were deposited onto the device in such a way that it was brought into contact with one of the source electrodes 101a, 101b A target electrolyte 105 consisting of 50 μl 0.1 mM sodium cloride was deposited onto the device in such a way that it was brought into contact with the target electrode 104. The electrolytes were physically separated from each other as well as from the overoxidized lines connecting the source and the target electrodes by an insulating layer 108.

Figure 10A:
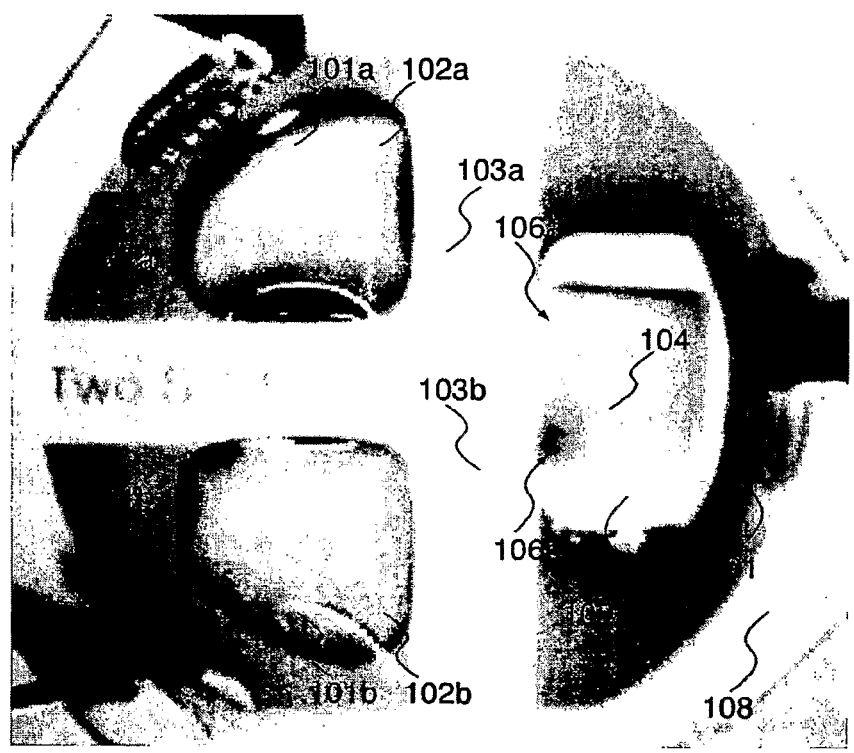
FIGS. 10a and 10b are top view photos of the experimental set up used for Example 2 and Example 3, respectively.

Ion transport from the added source electrolyte 102b to the target electrolyte 105 was performed by applying of a voltage between the source electrode 101b and the target electrode 104, across the ion-conductive channel 103b of the device. A voltage of 20 V was applied and the electronic current between the source and target electrode was recorded. The pumped $H^+$ ions were recorded with pH-paper which was placed on top of the electrolyte bottom surface and a USB-camera for recording the pictures. FIG. 10a shows the color change of the pH-paper where the $H^+$ ions were released from the ion passage surface 106b into the target electrolyte 105 edge. This shows that ions can be released locally by tailoring the width and cross-section of the ion conductive channel at the ion transport interface.

Example 3

Figure 10B:
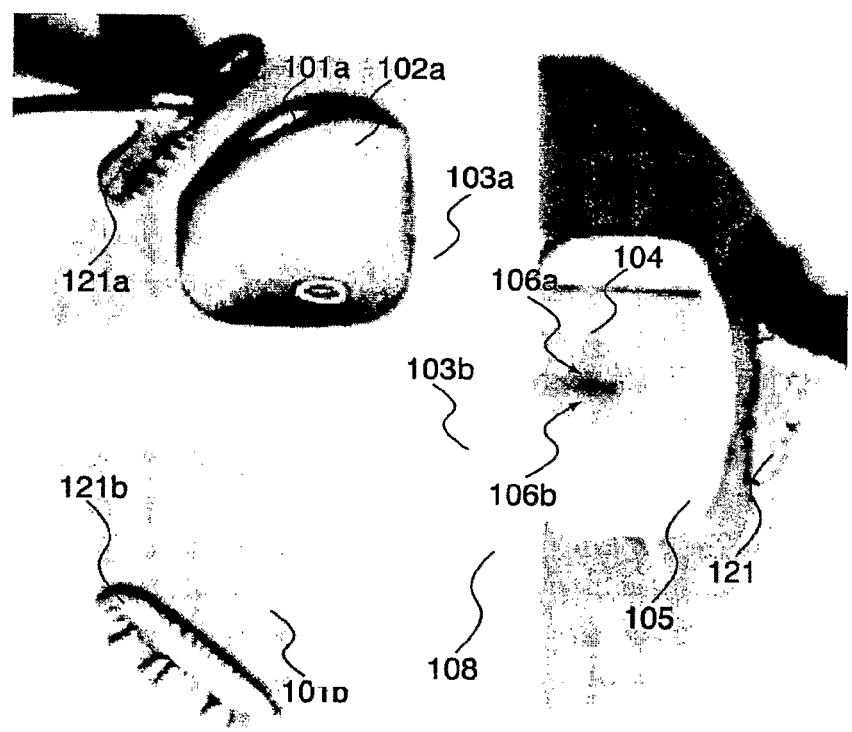

$H^+$ Transport Through a 100 μm Wide Ion Channel with Ion Transport Interface Inside the Target Electrode and Target Electrolyte The experiment was carried out in the same way as the experiment in example 2 except that in this experiment an ion pump device was used that has the ion transport interfaces 106a and 106b located inside the target electrode 104 and target electrolyte 105 (see FIG. 10b and compare FIG. 5).

As can be seen in FIG. 10b by the coloring of the pH paper, the $H^+$ ions were released at the ion transport interface 106a inside the target electrode 104 and target electrolyte 105. This shows how the ion transport interface and thus the release of ions to the target electrolyte 105 can be moved inside the target electrolyte 105.

In this experiment the electrolyte 102b was not added.

Example 4

Acetylcholine Transport and cell Stimulation Through a 10 μm Wide Ion Channel

The experiment was performed with a device fabricated as described in Preparatory Example 1 and as generally described in FIG. 4a, that is a ion pump device comprising two PEDOT:PSS source electrodes, one PEDOT:PSS waste electrode and one PEDOT:PSS target electrode. The ion-conductive channel in the form of 200, 50 and 10 μm wide overoxidized lines of PEDOT:PSS, obtained as described in Preparatory Example 1, went from both source electrodes into a merging point with the waste channel and forming a single ion channel which in its turn connected to the target electrode. A solution of 40 µl of a source electrolyte consisting of 0.1 M acetylcholine chloride was deposited onto the device in such a way that it was brought into contact with one of the source electrodes. A solution of 40 µl of a target electrolyte consisting of 0.1 M sodium chloride was deposited onto the device in such a way that it was brought into contact with the target electrode. The electrolytes were physically separated from each other as well as from the overoxidized line connecting the source and the target electrodes. Ion transport from the added source electrolyte to the target electrolyte was performed by applying a voltage between the source and the target electrodes, across the ion-conductive channel of the device. Voltages of 20 V and 40 V were applied for different time periods and the electronic current between the source and target electrode was recorded. The resulting increase in acetylcholine ion concentration in the target electrolyte was measured and is presented in FIG. 11a along with typical currents. It shows how the acetylcholine concentration increase linearly with time and how the current is close to constant. FIG. 11b shows the correlation between the transported amount of acetylcholine and total charge (which is the measured electronic current multiplied by the applied time).

For identical devices solutions of 40 µl of source electrolyte consisting of 0.1 M acetylcholine chloride was deposited onto the devices in such a way that it was brought into contact with one of the source electrodes. Solutions of 40 µl of waste electrolyte consisting of 0.1 M sodium chloride was deposited onto the devices in such a way that it was brought into contact with the waste electrode. Solution of 40 µl of target electrolyte consisting of a 1:1 mixture of Eagle's Minimum Essential Medium (EMEM) and F12 medium supplemented to final concentrations of 10% fetal bovine serum, 2 mM L-glutamine, 1% non-essential amino acids, 100 U/mL penicillin, 0.1 mg/mL streptomycin and 1% Hepes was deposited onto the devices in such a way that it was brought into contact with the target electrodes. Human neuroblastoma SH-SY5Y cells were cultured on the target electrodes and prepare for $Ca^{2+}$ recordings by incubation with the membrane-permeable $Ca^{2+}$-sensitive dye FURA-2 AM (2 µM) and 0.02% pluronic acid for 1 h in 37° C. in the dark. After 1 h in a 37° C. humified incubator, FURA-2 AM was replaced with 50 µl fresh cell media. First, 20V was applied between the source and waste electrodes to load the ion channel system with acetylcholine. Next a voltage was applied between the source and target electrodes to initiate acetylcholine transport and stimulate cells. The cell stimulation was recorded by changes of the intracellular calcium concentration. FIG. 11c shows how the amplitude of the voltage can modulate amplitude and slope in the cellular response. FIG. 11d shows how short pulses of acetylcholine can stimulate cells close to the transport interface 106 while leaving cells further away irresponsive.

The invention claimed is:

1. A device for electrically controlled transport of ions between a source and a target electrolyte, comprising:
   a first source electrode and a first target electrode, each capable of conducting ions and electrons, wherein said source electrode is arranged to receive ions from said source electrolyte and said target electrode is arranged to release ions to said target electrolyte, and
   means for retaining one of said source and target electrolytes on the device, which means are arranged such that each electrolyte is in contact with one of said electrodes, and a first ion-conductive channel, arranged to receive ions from said source electrode, to release ions to said target electrode and to provide an ionic connection between said source and said target electrodes,
   wherein said electrodes and said ion-conductive channel are formed of solid or semi-solid materials which are directly or indirectly attached to a support, further comprising means for limiting an electronic current between said source and said target electrodes, such that at least after a voltage is applied across said channel a potential difference between said source and target electrodes is maintained, which effects ion transport from said source to said target electrode,
   wherein the cross-sectional area of the interface between said ion-conductive channel and one of said electrodes is within the range of about 1 nm2 to about 10 mm2,
   the device further comprising an ion conductive waste channel and a waste electrode, which channel is ionically connected to said ion-conductive channel and to said waste electrode, and
   further comprising means for limiting an electronic current between said source and said waste electrodes, such that at least after a voltage is applied across said waste channel a potential difference between said source and waste electrodes is maintained, which effects ion transport in the direction from said source electrode to said waste channel.

2. A device according to claim 1, wherein an ion passage surface area of one of said electrodes is within the range of about 1 nm2 to about 10 mm2.

3. A device according to claim 1, further comprising ion isolative means covering a surface portion of the ion conductive channel.

4. A device according to claim 3, wherein the ion isolative means are arranged to define the spatial extension of said ion passage surface.

5. A device according to claim 3, wherein said means for retaining the electrolyte is arranged to retain the electrolyte in such a manner that at least a portion of the ion isolative means is sandwiched between the ion conductive channel and the electrolyte.

6. A device according to claim 1, further comprising at least one additional ion-conductive channel, spatially separated from said first ion-conductive channel, which at least one additional ion-conductive channel is arranged to receive ions from said source electrode, arranged to release ions to said target electrode and to provide an additional ionic connection between said source and target electrodes.

7. A device according to claim 1, further comprising an ion conductive flush channel and a flush electrode, which channel is ionically connected to said ion-conductive channel and to said flush electrode upstream of said enlarged portion, and further comprising means for limiting an electronic current between said target and said flush electrode, such that at least after a voltage is applied across said flush channel a potential difference between said target and flush electrodes is maintained, which effects ion transport in the direction from said flush electrode to said target electrode.

8. A device according to claim 1, wherein said electrodes and said ion-conductive channel is arranged as a unitary element, and preferably formed of the same material.

9. A device according to claim 1, wherein the length of the ion conductive channel is within the range of about 5 µm to 3 dm.

10. A device for electrically controlled transport of ions between a source and a target electrolyte, comprising:
   a first source electrode and a first target electrode, each capable of conducting ions and electrons, wherein said source electrode is arranged to receive ions from said source electrolyte and said target electrode is arranged to release ions to said target electrolyte, and means for retaining one of said source and target electrolytes on the device, which means are arranged such that each electrolyte is in contact with one of said electrodes, and a first ion-conductive channel, arranged to receive ions from said source electrode, to release ions to said target electrode and to provide an ionic connection between said source and said target electrodes, wherein said electrodes and said ion-conductive channel are formed of solid or semi-solid materials which are directly or indirectly attached to a support, further comprising means for limiting an electronic current between said source and said target electrodes, such that at least after a voltage is applied across said channel a potential difference between said source and target electrodes is maintained, which effects ion transport from said source to said target electrode, wherein the cross-sectional area of the interface between said ion-conductive channel and one of said electrodes is within the range of about 1 nm2 to about 10 mm2, wherein said ion conductive channel is arranged to branch out into at least a first and a second ion conductive channel portion which channel portions are spatially separated from each other, the device further comprising a second target electrode having a second ion passage surface, spatially separated from said first ion passage surface and arranged to be in ionic contact with an electrolyte, and means for limiting an electronic current between said source and said second target electrodes, such that at least after a voltage is applied across said second ion conductive channel portion a potential difference between said source and second target electrodes is maintained, which effects ion transport from said source to said second target electrode, and wherein said first ion passage surface is arranged to transmit ions from said first channel portion, and said second ion passage surface is arranged to transmit ions from said second channel portion.

11. A device according to claim 10, wherein said second ion passage surface is arranged to be in ionic contact with said target electrolyte.

12. A device according to claim 10, wherein said second ion passage surface is arranged to be in ionic contact with an electrolyte spatially separated from said target electrolyte.

13. A device for electrically controlled transport of ions between a source and a target electrolyte, comprising:
a first source electrode and a first target electrode, each capable of conducting ions and electrons, wherein said source electrode is arranged to receive ions from said source electrolyte and said target electrode is arranged to release ions to said target electrolyte, and means for retaining one of said source and target electrolytes on the device, which means are arranged such that each electrolyte is in contact with one of said electrodes, and a first ion-conductive channel, arranged to receive ions from said source electrode, to release ions to said target electrode and to provide an ionic connection between said source and said target electrodes, wherein said electrodes and said ion-conductive channel are formed of solid or semi-solid materials which are directly or indirectly attached to a support, further comprising means for limiting an electronic current between said source and said target electrodes, such that at least after a voltage is applied across said channel a potential difference between said source and target electrodes is maintained, which effects ion transport from said source to said target electrode, wherein the cross-sectional area of the interface between said ion-conductive channel and one of said electrodes is within the range of about 1 nm2 to about 10 mm2, the device further comprising:
at least one additional ion conductive channel,
at least one additional ion conductive source electrode, each comprising an ion passage surface,
means for retaining a source electrolyte in ionic contact with each of said at least one ion passage surface,
wherein a first portion of each of said at least one additional ion conductive channel is arranged in ionic contact with said first ion conductive channel, and wherein a second portion of each of said at least one additional ion conductive channel is arranged in ionic contact with one of said at least one additional ion conductive source electrodes, respectively, further comprising means for limiting an electronic current between said target electrode and each of said at least one additional source electrode, such that at least after a voltage is applied across a respective one of said at least one additional ion conductive channel, a potential difference between a source and a target electrode is maintained, which effects ion transport from said source to said target electrode.

14. A device according to claim 13, wherein said first ion conductive channel and said at least one additional ion conductive channel further comprise a common point of intersection.

15. A device for electrically controlled transport of ions between a source and a target electrolyte, comprising:
a first source electrode and a first target electrode, each capable of conducting ions and electrons, wherein said source electrode is arranged to receive ions from said source electrolyte and said target electrode is arranged to release ions to said target electrolyte, and means for retaining one of said source and target electrolytes on the device, which means are arranged such that each electrolyte is in contact with one of said electrodes, and a first ion-conductive channel, arranged to receive ions from said source electrode, to release ions to said target electrode and to provide an ionic connection between said source and said target electrodes, wherein said electrodes and said ion-conductive channel are formed of solid or semi-solid materials which are directly or indirectly attached to a support, further comprising means for limiting an electronic current between said source and said target electrodes, such that at least after a voltage is applied across said channel a potential difference between said source and target electrodes is maintained, which effects ion transport from said source to said target electrode, wherein the cross-sectional area of the interface between said ion-conductive channel and one of said electrodes is within the range of about 1 nm2 to about 10 mm2, the device further comprising
a first and a second additional ion conductive channel,
an additional ion conductive source electrode, comprising an ion passage surface,
an additional ion conductive target electrode, comprising an ion passage surface,
means for retaining an additional source electrolyte in ionic contact with said ion passage surface of said additional source electrode,
means for retaining an additional target electrolyte in ionic contact with said ion passage surface of said additional target electrode, wherein said first ion conductive channel is arranged in ionic contact with both said additional source electrode and said first target electrode, and wherein said second ion conductive channel is arranged in ionic contact with both said first source electrode and said additional target electrode, further comprising means for limiting an electronic current between said first source electrode and each of said first and additional target electrodes and, for limiting an electronic current between said additional source electrode and each of said first and additional target electrodes, such that at least after a voltage is applied across a respective one of said first and additional ion conductive channels a potential difference between a respective source and a target electrode is maintained, which effects ion transport from said source to said target electrode.

* * * * *